United States Patent
Panousis et al.

(10) Patent No.: US 9,617,329 B2
(45) Date of Patent: Apr. 11, 2017

(54) METHOD OF CLONING NUCLEIC ACID

(75) Inventors: Con Panousis, Parkville (AU);
Chao-Guang Chen, Parkville (AU)

(73) Assignee: CSL Limited, Parkville, Victoria (AU)

( * ) Notice: Subject to any disclaimer, the term of this patent is extended or adjusted under 35 U.S.C. 154(b) by 183 days.

(21) Appl. No.: 13/877,213

(22) PCT Filed: Oct. 3, 2011

(86) PCT No.: PCT/AU2011/001260
§ 371 (c)(1),
(2), (4) Date: Oct. 15, 2013

(87) PCT Pub. No.: WO2012/040793
PCT Pub. Date: Apr. 5, 2012

(65) Prior Publication Data
US 2014/0030761 A1   Jan. 30, 2014

(30) Foreign Application Priority Data
Oct. 1, 2010   (AU) ................................ 2010904430

(51) Int. Cl.
| | | |
|---|---|---|
| *C12P 19/34* | (2006.01) | |
| *C07K 16/00* | (2006.01) | |
| *C12N 15/65* | (2006.01) | |
| *G01N 33/563* | (2006.01) | |

(52) U.S. Cl.
CPC .............. *C07K 16/00* (2013.01); *C12N 15/65* (2013.01); *G01N 33/563* (2013.01)

(58) Field of Classification Search
CPC ...................................................... C12P 19/34
See application file for complete search history.

(56) References Cited

U.S. PATENT DOCUMENTS 6,174,708 B1 *   1/2001   Sodoyer et al. ............. 435/91.1

FOREIGN PATENT DOCUMENTS

| WO | WO 95/21914 A1 | 8/1995 |
| WO | WO 03/048306 A2 | 6/2003 |
| WO | WO 03/106684 A2 | 12/2003 |

OTHER PUBLICATIONS

Itaya et al. 1997; Experimental surgery to create subgenomes of Bacillus subtilis 168. PNAS 94:5378-5382.*
Karu et al. 1995; Recombinant antibody technology. ILAR Journal 37(3): 132-141.*
Engler et al. 2009; Golden Gate Shuffling: A one-pot DNA suffling method based on type II restriction enzymes. Plos One 4(5): e5553 comprising pp. 1-9.*
In-Fusion Cloning FAQs, 2015, on the web at clontech.com/US/Products/Cloning_and_Competent_Cells/Cloning_Resources/FAQs/In-Fusion_Cloning.*
International Preliminary Report on Patentability and Written Opinion dated Apr. 11, 2013 issued in PCT/AU2011/001260.
Tsuge, Kenji et al., "One step assembly of multiple DNA fragments with a designed order and orientation in Bacillus subtilis plasmid", Nucleic Acids Research (2003), vol. 31, No. 21, p. e133.
Berrow, Nick S., "A versatile ligation-independent cloning method suitable for high-throughput expression screening applications", Nucleic Acids Research (2007), vol. 35, No. 6, p. e45.
Zhu, Baogong et al., "In-Fusion assembly: seamless engineering of multidomain fusion proteins, modular vectors, and mutations", BioTechniques (Sep. 2007), vol. 43, No. 3, pp. 354-359.

* cited by examiner

*Primary Examiner* — Karen Cochrane Carlson
(74) *Attorney, Agent, or Firm* — Scully, Scott, Murphy & Presser, P.C.

(57) ABSTRACT

The present disclosure provides methods for producing expression constructs comprising linking a plurality of unlinked nucleic acids, including a nucleic acid encoding a marker protein.

21 Claims, 9 Drawing Sheets

A):

B):

| Selection method | Colony count | - Insert | + Inserts |
|---|---|---|---|
| Traditional selection: | Total colonies | 1154 | 753 |
| Amp | Clones with Insert | 0/2 | 3/7 |
| INTAPS selection: | Total colonies | 0 | 168 |
| Cm | Clones with Insert | NA | 7/7 |

A:

B:

METHOD OF CLONING NUCLEIC ACID

RELATED APPLICATION DATA

The present application is a '371 application of International Application No. PCT/AU2011/001260, which claims priority from Australian Patent Application No. 2010904430 entitled "Method of cloning nucleic acid" filed on 1 Oct. 2010, the contents of each of which are incorporated herein by reference in their entirety.

SEQUENCE LISTING

A Sequence Listing is filed in electronic form as part of this application and is hereby incorporated by referenced in its entirety.

FIELD

The present disclosure relates generally to methods for cloning nucleic acids and/or methods for expressing or producing polypeptides.

BACKGROUND

Over the past 10 to 15 years, there has been a surge in interest in therapeutic proteins. For example, in 2007, therapeutic monoclonal antibody sales in USA exceeded $14 billion, with a year on year growth rate of 22%. Other therapeutic proteins that have gained significant interest are Fc-fusion proteins (e.g., comprising an extracellular domain of a receptor fused to an antibody Fc region), such as etanercept, which had worldwide sales of US$3.5 billion in 2009 alone.

Recently, the initial steps in producing new therapeutic proteins have involved screening large numbers of proteins for desirable properties. In the case of antibodies, this often involves screening antibody variable region containing proteins, such as scFv and Fab fragments, to identify those capable of binding to a target antigen with high affinity. The isolated variable region containing proteins may also undergo numerous rounds of mutation and rescreening to improve the affinity of the protein for the antigen. Similarly, a protein that is to be fused to a Fc region may undergo numerous rounds of mutation and screening to select proteins having desirable proteins, such as specificity for a ligand or reduced off-target effects.

After isolating proteins of interest, these proteins must be reformatted into an expression vector that contains the regions necessary to produce a complete antibody or Fc fusion. Moreover, if the protein is to be expressed in mammalian cells, e.g., to ensure correct folding and glycosylation, the expression vector must contain the requisite elements for expression. This reformatting step can be complicated and time consuming. For example, the proteins to be reformatted are often variable in sequence making polymerase chain reaction (PCR) amplification and restriction endonuclease digestion difficult. Furthermore, in the case of antibodies, there is often a requirement for multiple rounds of cloning since the light chain and heavy chain are encoded by separate nucleic acids.

Another difficulty with reformatting antibodies using restriction endonuclease-based technology arises from the multiple cloning site in an expression vector which can encode additional amino acids on either or both termini of the protein. This may have undesirable effects both from a functional point-of-view and may form immunogenic epitopes in the resulting protein.

A further difficulty with standard reformatting techniques is in the use of multiple vectors for expressing antibodies, i.e., a vector for expressing the light chain and a vector for expressing the heavy chain. The use of multiple vectors adds a level of complexity that makes it difficult to perform reformatting techniques in a high throughput or automated manner. For example, such techniques often require producing each expression vector independently and confirming that the correct sequence is inserted into each vector. A further difficulty is encountered when attempting to express the antibody in so far as different numbers of copies of each vector can be inserted into a transfected cell resulting in different levels of expression of each chain and sub-optimal production levels.

As a result of the difficulties with using two vectors, it is desirable to insert sequences encoding antibody light and heavy chains into a single vector. Currently used methods usually require multiple steps, e.g., first cloning a heavy chain encoding sequence and then subsequently cloning light chain encoding sequence. The requirement for multiple cloning steps makes these protocols laborious and they are not readily amenable to automation.

A further difficulty arising from the methods described above arises from the use of cloning methods involving growing bacterial cells on a solid medium to select for individual clones and identify those comprising the correct inserted DNA, e.g., encoding an antibody chain. In an effort to facilitate identification of clones containing inserted DNA, traditional methods make use of complementation of a dysfunctional reporter gene (e.g., β-galactosidase) and/or use of an expression vector comprising a gene that confers resistance to an antibiotic. However, these methods suffer from problems of high background levels resulting from vector self-ligation, i.e., without an inserted nucleic acid, and/or uncleaved vector. As a result of this high level of background, it is often necessary to physically isolate and screen numerous clones to identify one containing the correct sequence. These screening methods are time-consuming and not readily amenable to automation.

The skilled artisan will be aware from the foregoing that there is a need in the art for simplified techniques for cloning nucleic acids for expression, e.g., for reformatting antibody encoding sequences to express entire antibodies. Desirably, such a technique is amenable to use in high-throughput or automated techniques.

SUMMARY

The inventors have now produced a method and reagents that permit them to readily clone nucleic acids encoding polypeptides that can be adapted to automation and/or high-throughput techniques. These methods can be used to clone nucleic acid encoding a single polypeptide, multiple polypeptides or even component polypeptides of a multimeric protein. In developing this method, the inventors have cloned numerous sequences encoding antibody heavy and light chain variable regions as examples of component polypeptides of multimeric proteins, i.e., antibodies. The inventors have shown that the method can be performed in a high throughput manner by cloning nucleic acids encoding in excess of 80 antibodies in parallel. This demonstrates that the method is readily scalable from producing single expression constructs to producing large numbers of expression constructs in parallel. The inventors have also shown that the method is readily applicable to reformatting antibody fragments into complete antibodies, having now reformatted in excess of 1000 antibodies. The method produced by the disclosure permits cloning of nucleic acids encoding one or multiple polypeptides into a single vector, and selection of cells comprising the correctly cloned nucleic acids. The inventors have also demonstrated that the method can be performed in solution, i.e., without a requirement to grow clones on a solid medium and select and screen those clones. This method also permits the nucleic acids to be operably linked to nucleic acids, e.g., promoters and/or enhancers, so as facilitate expression. This cloning method can be performed in a cloning cycle. The method produced by the inventors does not require multiple cloning cycles and/or does not make use of multiple vectors. Thus, the method produced by the inventors is readily adaptable to high through-put and/or automated cloning techniques.

Accordingly, the present disclosure provides a method for producing an expression construct capable of expressing a polypeptide, the method comprising linking the following unlinked nucleic acids:
(i) a nucleic acid encoding the polypeptide; and
(ii) a nucleic acid encoding a marker protein that facilitates detection and/or isolation of a cells expressing the marker protein; and
(iii) an expression vector, which does not comprise a nucleic acid encoding the marker protein encoded by the nucleic acid at (ii),
such that the nucleic acid encoding the marker protein is positioned between the nucleic acid encoding the polypeptide and the expression vector.

As exemplified herein, the method of the present disclosure is also useful for cloning a plurality of nucleic acids each encoding a polypeptide into a single expression vector. Accordingly, the present disclosure provides a method for producing an expression construct capable of expressing a plurality of polypeptides, the method comprising linking the following unlinked nucleic acids:
(i) a nucleic acid encoding a first polypeptide;
(ii) a nucleic acid encoding a second polypeptide; and
(iii) a nucleic acid encoding a marker protein that facilitates detection and/or isolation of a cells expressing the marker protein; and
(iv) an expression vector, which does not comprise a nucleic acid encoding the marker protein encoded by the nucleic acid at (iii).

When the nucleic acids are linked, the nucleic acid encoding the maker protein can be positioned between the nucleic acid encoding the first polypeptide and the nucleic acid encoding the second polypeptide or 5' to those nucleic acids or 3' to those nucleic acids (e.g., between the nucleic acid encoding one of the polypeptides and the expression vector).

The present disclosure additionally, or alternatively provides a method for producing an expression construct capable of expressing a plurality of polypeptides, the method comprising linking the following unlinked nucleic acids:
(i) a nucleic acid encoding the first polypeptide;
(ii) a nucleic acid encoding a marker protein that facilitates detection and/or isolation of a cells expressing the marker protein; and
(iii) a nucleic acid encoding the second polypeptide,
such that the nucleic acid encoding the marker protein is positioned between the first and second nucleic acids.

Optionally, the nucleic acids are linked to an expression vector, which does not comprise a nucleic acid encoding the marker protein encoded by the nucleic acid at (ii), e.g., in the same cloning cycle as the nucleic acids are linked.

One advantage of placing the nucleic acid encoding the marker protein between the nucleic acids encoding the polypeptides is that the inventors can include additional components, e.g., promoter and/or secretion signal that are to be operably linked to the nucleic acid encoding the second polypeptide and/or a sequence encoding a further polypeptide to be fused to either the first or second polypeptide. The method can also be performed using nucleic acids adapted to be capable of linking only in the recited order and a vector that is adapted to be capable of linking only to the correctly oriented other nucleic acids, making it possible to select for clones expressing the marker protein, which will also comprise nucleic acids encoding the first and second polypeptides.

In one example, the nucleic acids are adapted so as to permit linking. For example one or both of the termini of the nucleic acids comprise a single stranded region that is complementary to a single stranded region of another of the nucleic acids. Alternatively, the sequence at a terminus of one nucleic acid (e.g., the 15 or 12 or 10 or 9 or 8 or 7 or 6 or 5 terminal nucleotides) is sufficiently homologous (or is identical to) the sequence at a terminus of another nucleic acid so as to permit homologous recombination in a cell (e.g., the sequences of the termini are at least about 80% identical or 90% identical or 95% identical or 99% identical or 100% identical).

In one example, the nucleic acids are adapted so as to reduce the likelihood of production of an expression construct lacking one or more of the nucleic acids. For example, the sequence at each terminus of each nucleic acid is adapted so as to facilitate linkage to only one of the other nucleic acid.

It will be apparent to the skilled person from the foregoing that the method of the present disclosure permits positive selection of an expression construct encoding a polypeptide or a plurality of polypeptides. This is because when the nucleic acids are linked, expression of the marker protein permits selection of the construct (or cells or particles comprising same) expressing the polypeptide(s). In contrast, constructs that do not comprise all of the nucleic acids will not express the marker protein and will not facilitate selection.

The method described herein for cloning a plurality of polypeptides is readily adaptable for cloning nucleic acids encoding two or three or four or five or six or seven or eight or nine or ten or more polypeptides.

In one example, the expressed polypeptides associate to form a multimeric protein.

In one example, the nucleic acids are linked together using ligase independent cloning. In an exemplary form of this disclosure any two nucleic acids to be linked comprise a region that is identical or substantially identical (e.g., differing by one or two or three nucleotides) at a terminus, e.g., a nucleic acid encoding a marker protein comprises a region that is identical or substantially identical to a region of a nucleic acid encoding a polypeptide. In one example, the identical or substantially identical regions are between 5 and 100 nucleotides long, such as about 15 nucleotides long. In one example, the method additionally comprises contacting the nucleic acids with a polymerase having 3'-5' exonuclease activity, e.g., from a poxvirus, e.g., from Vaccinia virus under conditions sufficient for the polymerase to link the nucleic acids.

In one example, the method additionally comprises contacting the nucleic acids with a single strand DNA binding protein, such as vaccinia single-stranded DNA-binding protein (gpI3L).

The present disclosure also contemplates the use of ligase-based cloning techniques. In this regard, the inventors have demonstrated that the method described herein is readily adaptable to ligase-based cloning techniques.

The present disclosure also contemplates using recombination, e.g., in a cell, to link the nucleic acids. For example, the nucleic acids each comprise a region that is identical or substantially identical to a region of one of the other nucleic acids. Upon introduction of the nucleic acid into a cell homologous recombination occurs between the identical or substantially identical regions thereby linking the nucleic acids.

In one example, the nucleic acids (i), (ii) and (iii) (and (iv), if present) are linked in a single cloning cycle.

In one example, the nucleic acids (i), (ii) and (iii) (and (iv), if present) are linked in a single reaction vessel or in a single cell.

In an exemplary form of the disclosure the vector comprises a nucleic acid encoding a further polypeptide that is to be expressed as a fusion with at least one of the polypeptides. For example, the vector comprises a sequence encoding an antibody heavy chain region, such as a Fc region and/or a heavy chain constant region 1 ($C_H1$) and Fc region, which is to be expressed as a fusion with at least one of the polypeptides. The further polypeptide may be any polypeptide, including a tag (e.g. a histidine tag or a FLAG tag) or a therapeutic polypeptide (e.g. a polypeptide comprising an antibody variable region) or a half-life extending polypeptide (e.g., albumin or an albumin binding polypeptide) or a toxin.

In one example, the first and second nucleic acids are each operably linked to promoters.

In accordance with this example, the nucleic acid encoding the marker protein can additionally comprise a promoter that is to become operably linked to at least one of the nucleic acids encoding a polypeptide.

The nucleic acid encoding the marker protein can comprise additional features, such as, a polyadenylation signal to be operably linked to a nucleic acid encoding a polypeptide and/or a region encoding a further polypeptide to be expressed as a fusion at least one of the polypeptides (e.g., a light chain constant region ($C_L$).

Similarly, the nucleic acid(s) encoding the polypeptide(s) can comprise additional features. For example, in a construct comprising two or more nucleic acids encoding polypeptides, one of those nucleic acids can comprise an internal ribosome entry site (IRES) that is positioned such that when the nucleic acids are linked it is between the polypeptide encoding regions. In this manner, two distinct polypeptides can be expressed using a single promoter.

An exemplary promoter applicable to any example of the disclosure is a promoter from cytomegalovirus (CMV, such as a cytomegalovirus immediate early promoter (referred to herein as pCMV). An exemplary polyadenylation signal applicable to any example of the disclosure is a bovine growth hormone polyadenylation signal (referred to herein as BGHpA).

In one example, the marker protein confers resistance to a toxic compound on a cell in which it is expressed. For example, the marker protein confers resistance to an antibiotic to a cell in which it is expressed. In one example, the marker protein confers resistance to chloroamphenicol or Zeocin (e.g., confers resistance on a bacterial cell). It will be apparent to the skilled artisan, that a cell in which the marker protein is not expressed is not resistant to the toxic compound.

The present disclosure also contemplates use of a marker protein that permits detection of a cell expressing the protein, e.g. a fluorescent protein and/or a protein that confers a growth advantage on an auxotrophic cell, e.g., by conferring the ability to produce an essential amino acid and/or a protein that metabolizes a substrate to produce a detectable compound.

The skilled artisan will understand from the description herein, that the nucleic acid encoding the marker protein will be operably linked to a promoter that controls expression of the marker protein in a cell.

In one example, the nucleic acid encoding the marker protein additionally comprises the operably linked promoter.

An expression construct of the present disclosure can comprise a plurality of nucleic acids encoding marker proteins. For example, a method of the disclosure may be performed using a nucleic acid encoding a marker protein and an expression vector comprising a further nucleic acid encoding a marker protein (which is different to the marker protein encoded by the nucleic acid). In this manner a cell comprising the expression construct can be identified or isolated by selecting for expression of both marker proteins.

In one exemplary form of the disclosure, the encoded polypeptide(s) comprise antibody variable region(s). In the situation of a construct encoding a plurality of polypeptides, a first polypeptide comprises an antibody light chain variable region ($V_L$) and, optionally a $C_L$ and a second polypeptide comprises an antibody heavy chain variable region ($V_H$).

In one example, a method of the disclosure comprises linking the following unlinked nucleic acids:
(i) a nucleic acid encoding an antibody heavy chain variable region ($V_H$);
(ii) a nucleic acid encoding a marker protein that facilitates detection and/or isolation of a cells expressing the marker protein and a promoter; and
(iii) an expression vector comprising a sequence encoding one or more antibody heavy chain constant regions, wherein the vector does not comprise a nucleic acid encoding the marker protein encoded by the nucleic acid at (ii);
such that:
(a) the promoter and the nucleic acid encoding the $V_H$ are operably linked; and
(b) the nucleic acid encoding the $V_H$ and the sequence encoding one or more antibody heavy chain constant regions are linked so as to encode a functional fusion protein.

In another example, a method of the present disclosure comprises linking the following unlinked nucleic acids:
(i) a nucleic acid encoding an antibody light chain variable region ($V_L$);
(ii) a nucleic acid encoding a marker protein that facilitates detection and/or isolation of a cells expressing the marker protein; and
(iii) an expression vector comprising a promoter, which does not comprise a nucleic acid encoding the marker protein encoded by the nucleic acid at (ii),
such that:
(a) the promoter and the nucleic acid encoding the $V_L$ are operably linked; and
(b) the nucleic acid encoding the marker protein is positioned between the nucleic acid encoding the $V_L$ and the expression vector.

In one example, the nucleic acid encoding the marker protein additionally includes a polyadenylation signal, which following linking of the nucleic acids is operably linked to the nucleic acid encoding the $V_L$.

In an additional example, wherein the nucleic acids encoding the $V_L$ additionally comprises a sequence encoding a light chain constant region positioned 3' to the sequence encoding the $V_L$.

In one example, a method of the present disclosure comprises linking the following unlinked nucleic acids:
(i) a first nucleic acid encoding an antibody $V_L$ and a $C_L$;
(ii) a nucleic acid encoding a marker protein that facilitates detection and/or isolation of a cells expressing the marker protein and a first promoter;
(iii) a second nucleic acid encoding an antibody $V_H$; and
(iv) an expression vector comprising a second promoter and a sequence encoding one or more antibody heavy chain constant regions (such as, comprising a heavy chain constant region 1 ($C_H1$) and a Fc region), wherein the vector does not comprise a nucleic acid encoding the marker protein encoded by the nucleic acid at (ii);
such that:
(a) the second promoter and first nucleic acid are operably linked;
(b) the nucleic acid encoding the marker protein is positioned between the first and second nucleic acids such that the first promoter is operably linked to the second nucleic acid;
(c) the second nucleic acid and the sequence encoding one or more antibody heavy chain constant regions are linked so as to encode a functional fusion protein.

In one example, the nucleic acid encoding the marker protein additionally comprises a polyadenylation signal that is operably linked to the first nucleic acid.

In one example, the nucleic acid encoding the marker protein comprises a secretion signal 3' to the promoter that is operably linked to the second nucleic acid.

In one example, the nucleic acid encoding the $V_H$ and/or the $V_L$ is isolated from a cell or particle displaying on its surface the $V_H$ and/or the $V_L$. For example, the $V_H$ and/or $V_L$ are expressed on the surface of a phage (e.g., in the form of a scFv, Fv or Fab). In accordance with this example, the method additionally comprises isolating and/or amplifying nucleic acid encoding the $V_H$ and/or $V_L$ (and, if present, $C_H1$ and/or $C_L$) and then performing a method of the disclosure with the isolated/amplified nucleic acid.

In one example, the method comprises:
(i) screening a library (or plurality) of cells or particles displaying on their surfaces a $V_H$ and/or the $V_L$ to identify or isolate those cells or particles displaying a $V_H$ and/or the $V_L$ having a biological activity of interest, e.g., capable of binding to an antigen;
(ii) isolating and/or amplifying nucleic acid encoding the $V_H$ and/or $V_L$ (and, if present, $C_H1$ and/or $C_L$) displayed on the isolated/identified cells/particles;
(iii) and performing a method of the disclosure with the isolated/amplified nucleic acid.

In one example, a method of the present disclosure additionally comprises introducing the expression construct into a cell. In one example, the cell is a bacterial cell, e.g., an E. coli cell.

Alternatively, or additionally, the method comprises introducing a region of the expression construct comprising at least the nucleic acid(s) encoding the polypeptide(s) into a cell. In this regard, the method can additionally comprise producing or obtaining the region of the expression construct, e.g., by cleavage with an endonuclease and/or amplification (e.g., by PCR). The discussion herein in relation to cells comprising the expression construct shall be taken to apply mutatis mutandis to cells comprising a region of the expression construct.

In an additional example, a method of the present disclosure comprises selecting a cell comprising the expression construct. For example, the marker protein confers resistance to a toxic compound on a cell in which it is expressed, and a cell comprising the expression construct is selected by exposing the cell to the toxic compound.

The present inventors have demonstrated that the method of producing an expression vector of the present disclosure can be performed in solution, which can provide an advantage in terms of high-throughput methods and/or automation. Accordingly, in one example, a process for producing an expression construct of the present disclosure is performed in solution. In one example, a process for producing an expression construct of the present disclosure is performed without culturing or maintaining cells in or on a solid medium.

The inventors have also demonstrated that the method of the present disclosure is readily amenable to growing and selecting cells in or on a solid medium. Accordingly, in one example, a method of the disclosure comprises growing cells (e.g., bacterial cells) in or on a solid medium and/or selecting cells grown in or on a solid medium.

Following selection, the expression vector can be isolated from a cell and introduced into a new cell. For example, the expression vector can be produced and/or amplified in a bacterial cell (e.g., E. coli), isolated and introduced into another cell (e.g., a mammalian cell) for expression of the encoded polypeptide/protein. In accordance with this example, promoters operably linked to the nucleic acids encoding the polypeptides will be operable in cells in which expression is to take place.

A method as described herein according to any example can additionally comprise producing the first and second nucleic acids. For example, the first and second nucleic acids are produced by performing an amplification reaction, e.g., PCR.

As discussed herein, the present disclosure also provides a high-throughput method for producing expression constructs and/or cells comprising same. Accordingly, the present disclosure also provides a method of producing a plurality of expression constructs, comprising performing the method of the present disclosure a plurality of times in parallel, to thereby produce the plurality of expression constructs.

In one example, at least 5 expression constructs are produced, or at least 10 expression constructs are produced or at least 20 expression constructs are produced, or at lease 30 expression constructs are produced, or at least 40 expression constructs are produced, or at least 50 expression constructs are produced, or at least 60 expression constructs are produced, or at least 70 expression constructs are produced, or at least 80 expression constructs are produced, or at least 90 expression constructs are produced, or at least 100 expression constructs are produced, or at least 150 expression constructs are produced, or at least 200 expression constructs are produced.

In another example, a method of the present disclosure additionally comprises isolating a cell or particle comprising nucleic acids encoding polypeptide(s) or multimeric protein or fragments of said polypeptide/protein. For example, the method comprises isolating a phage comprising nucleic acids encoding antibody $V_L$ and $V_H$ that bind to an antigen.

The present disclosure also provides a method of producing an expression construct comprising obtaining the sequence of the polypeptide(s) encoded by the expression construct produced by performing a method described herein according to any example, producing a further expression construct encoding the polypeptide(s) and expressing the polypeptides. In one example, the method comprises introducing the further expression construct into a cell. In one example, the sequence(s) encoding the polypeptide(s) or fusion(s) thereof in the further expression construct are selected for preferential usage or enhanced expression in the cell, i.e., codon optimized. In this regard, codons encoding each amino acid within the polypeptide are analyzed and codons preferentially used by the cell are selected and used to produce the expression construct. Information on preferential codon usage is publically available.

In one example, a method of the disclosure comprises obtaining the sequence of the nucleic acid encoding the polypeptide(s) or fusion(s) thereof produced by performing a method described herein according to any example, producing a further expression construct comprising a sequence(s) encoding the polypeptide(s) or fusion(s) thereof and expressing the polypeptide(s). In one example, the method comprises introducing the further expression construct into a cell. In one example, the sequence(s) encoding the polypeptide(s) or fusion(s) thereof in the further expression construct are optimized or selected for enhanced expression in the cell, i.e., codon optimized.

In one example, a method of the disclosure comprises obtaining an expression construct produced by performing a method of the disclosure, introducing the expression construct into a cell and expressing the polypeptide.

The method of the present disclosure is useful for producing an expression construct for expressing any polypeptide. In one example, the polypeptide is a cytokine or a growth factor or a receptor or an extracellular domain or a receptor or a chemokine or a cluster of differentiation polypeptide or a mutein of any of the foregoing. The method of the present disclosure is also useful for cloning nucleic acids encoding any of the foregoing polypeptides in such a manner to be expressed as a fusion with a further polypeptide, e.g., a Fc domain or any other further polypeptide known in the art and/or described herein.

The expression construct produced by the present disclosure can express a plurality of polypeptides that are unrelated to one another or that interact with one another, e.g., Factor IX and PACE/furin.

In one example, a method of the present disclosure is useful for producing an expression construct encoding a polypeptide comprising an antibody variable region or a plurality thereof. Exemplary polypeptides include, a single $V_H$ or $V_L$ (e.g., a domain antibody), a heavy chain variable region from a heavy chain only antibody ($V_{HH}$), a scFv and higher order versions thereof (e.g., sc(Fv)$_2$, (scFv)$_2$ or sc(Fv')$_2$).

In another example, a method of the present disclosure is useful for producing a plurality of polypeptides that form a multimeric protein, such as, an antibody, a Fab, a Fv, a F(ab')$_2$, a diabody, a triabody or a tetrabody. Other multimeric proteins include, for example, Fc fusion proteins (e.g., multi-specific Fc fusion proteins) or T cell receptors or multimeric cytokines.

The present disclosure also provides an expression construct capable of expressing a plurality of polypeptides, the vector comprising the following components linked in 5'-3' order:

(i) a nucleic acid encoding a first polypeptide;
(ii) a nucleic acid encoding a marker protein that facilitates detection and/or isolation of a cells expressing the marker protein; and
(iii) a nucleic acid encoding a second polypeptide,
such that the nucleic acid encoding the marker protein is positioned between the first and second nucleic acids.

The present disclosure also provides an expression construct capable of expressing an antibody or antigen binding fragment thereof comprising the following components:
(i) a first promoter operably linked to a nucleic acid encoding a polypeptide comprising an antibody light chain variable region and an antibody light chain constant region;
(ii) a nucleic acid encoding a marker protein that facilitates detection and/or isolation of a cells expressing the marker protein; and
(iii) a second promoter operably linked to a nucleic acid encoding a polypeptide comprising an antibody heavy variable region and one or more antibody heavy chain constant regions,
wherein the nucleic acid encoding the marker protein is positioned between the first nucleic acid and the second promoter.

The present disclosure also provides a cell comprising the expression vector of the present disclosure or an expression construct produced by performing a method of the present disclosure. For example, the cell is a eukaryotic cell, such as a mammalian cell.

The present disclosure also provides a process for producing a polypeptide or a plurality of polypeptides comprising maintaining the expression construct produced by performing a method of the present disclosure or an expression construct of the present disclosure or a cell of the present disclosure under conditions such that the polypeptide is expressed.

The present disclosure also provides a process for producing a polypeptide or a plurality of polypeptides, the method comprising:
(i) obtaining an expression construct comprising a nucleic acid encoding the polypeptide(s), wherein the sequence of the nucleic acid encoding the polypeptide(s) was previously determined by performing a method described herein according to any example to produce an expression construct, determining the sequence encoding the polypeptide(s) in the expression construct, and producing a sequence encoding the polypeptide(s); and
(ii) expressing the polypeptide(s).

In one example, the method comprises introducing the expression construct into a cell and expressing the polypeptide.

The present disclosure also provides a process for producing a polypeptide or a plurality of polypeptides, the method comprising:
(i) obtaining a cell comprising an expression construct comprising a nucleic acid encoding the polypeptide(s), wherein the sequence of the nucleic acid encoding the polypeptide(s) was previously determined by performing a method described herein according to any example to produce an expression construct, determining the sequence encoding the polypeptide(s) in the expression construct, and producing a sequence encoding the polypeptide(s); and
(ii) expressing the polypeptide(s).

In one example, the process additionally comprises purifying the polypeptide or plurality polypeptides.

In one example, the polypeptide comprises a variable region of an antibody.

In one example, the plurality of polypeptides associate to form an antibody.

In one example, the process additionally comprises formulating the polypeptide (or plurality of polypeptides) into a pharmaceutical composition. For example, the method comprises combining the polypeptide (or plurality of polypeptides) with a pharmaceutically acceptable carrier.

BRIEF DESCRIPTION OF THE DRAWINGS

FIG. 3 Panel B is a table summarizing the number of *E. coli* colonies following transformation and selection as described in respect of FIG. 3 Panel A using either classical or INTAPS selection methods. Using INTAPS (Cm selection), no colonies were produced by the negative control containing only the cut vector DNA. In contrast 7 of the 7 randomly picked colonies from the insert/vector ligation transformation were shown to contain the correct insert by restriction endonuclease digestion. These data indicate that the cloning background from uncut or re-ligated vector DNA was reduced or eliminated.

DETAILED DESCRIPTION

General

Figure 1:
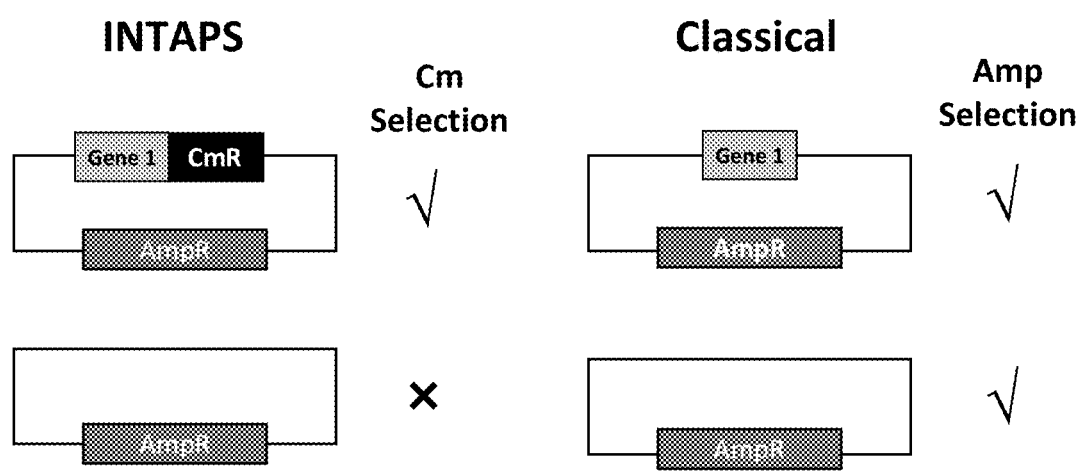
FIG. 1 is a graphical representation depicting a comparison between classical selection of recombinant plasmids and Insert-Tagged Positive Selection of recombinant plasmids. As depicted, classical selection permits selection whether or not an expression construct comprises a nucleic acid encoding a polypeptide of interest (Gene 1), whereas INTAPS permits selection for constructs comprising the nucleic acid and selection against those constructs not comprising the nucleic acid.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the exemplary description provided herein, which is intended for the purpose of exemplification only. Functionally-equivalent products, compositions and methods are clearly within the scope of the disclosure.

Any example herein shall be taken to apply mutatis mutandis to any other example unless specifically stated otherwise.

Any example in relation to a multimeric protein as described herein shall be taken to apply mutatis mutandis to an antibody unless specifically stated otherwise. For example, reference to a nucleic acid encoding a polypeptide will be taken to mean a nucleic acid encoding an antibody variable region.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SELECTED DEFINITIONS

The term "expression construct" is to be taken in its broadest context and includes a nucleic acid comprising one or more promoters operably linked with a nucleic acid encoding a polypeptide.

The term "expression vector" refers to a nucleic acid capable of maintaining and/or replicating nucleic acid in an expressible format. For example, an expression vector may comprise a plasmid, bacteriophage, phagemid, cosmid, virus sub-genomic or genomic fragment. Selection of appropriate vectors is within the knowledge of those having skill in the art.

The term "polypeptide" will be understood to mean a series of contiguous amino acids linked by peptide bonds.

The term "multimeric protein" shall be taken to mean a series of polypeptides covalently or non-covalently linked to one another (i.e., a polypeptide complex). For example, the series of polypeptides can be covalently linked using a suitable chemical or a disulphide bond. Examples of non-covalent bonds include hydrogen bonds, ionic bonds, Van der Waals forces, and hydrophobic interactions. In one example, the two polypeptides are different.

The term "unlinked nucleic acids" will be understood to mean that the nucleic acids are distinct molecules, i.e., are not joined to one another by a phosphodiester bond (in the context of DNA).

The term "single cloning cycle" will be understood to mean the process of combining and linking nucleic acids and introducing those nucleic acids into a cell. This term also encompasses producing and/or isolating the nucleic acids. This term does not extend to multiple consecutive rounds of combining and linking nucleic acids and introducing the nucleic acids into cells.

In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning two components such that one component affects the other. For example, a promoter is operably linked to a nucleic acid, when it is positioned relative to a nucleic acid such that expression of the nucleic acid is controlled by the promoter. A secretion signal is operably connected to a polypeptide when it is positioned such that it is capable of directing secretion of the polypeptide, e.g., linked at the amino terminus of the polypeptide.

As used herein, the term "antibody" shall be taken to mean a protein that comprises a variable region made up of a plurality of polypeptide chains, e.g., a light chain variable region ($V_L$) and a heavy chain variable region ($V_H$). An antibody also generally comprises constant domains, which can be arranged into a constant region or constant fragment or fragment crystallizable (Fc). Antibodies can bind specifically to one or a few closely related antigens. Generally, antibodies comprise a four-chain structure as their basic unit. Full-length antibodies comprise two heavy chains (approximately 50-70 kDa) covalently linked and two light chains (approximately 23 kDa each). A light chain generally comprises a variable region and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are approximately 110 amino acids in length) and one or more constant domains at the C-terminus. The constant domain of the light chain ($C_L$ which is approximately 110 amino acids in length) is aligned with and disulfide bonded to the first constant domain of the heavy chain ($C_H$ which is approximately 330-440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region can be identified between the $C_H1$ and Cm constant domains. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. In one example, the antibody is IgG, such as $IgG_3$. In one example, the antibody is a murine (mouse or rat) antibody or a primate (e.g., human) antibody. The term "antibody" also encompasses humanized antibodies, primatized antibodies, deimmunized antibodies, human antibodies and chimeric antibodies.

As used herein, "variable region" refers to the portions of the light and heavy chains of an antibody or immunoglobulin as defined herein that includes amino acid sequences of CDRs; i.e., CDR1, CDR2, and CDR3, and FRs. $V_H$ refers to the variable region of the heavy chain. $V_L$ refers to the variable region of the light chain. According to the methods used in this disclosure, the amino acid positions assigned to CDRs and FRs are defined according to Kabat *Sequences of Proteins of Immunological Interest*, National Institutes of Health, Bethesda, Md., 1987 and 1991. The skilled artisan will be readily able to use other numbering systems in the performance of this disclosure, e.g., the hypervariable loop numbering system of Chothia and Lesk *J. Mol. Biol.* 196: 901-917, 1987 and/or Chothia et al. *Nature* 342, 877-883, 1989 and/or Al-Lazikani et al., *J Mol Biol* 273, 927-948, 1997).

As used herein, the term "heavy chain variable region" or "$V_H$" shall be taken to mean a protein capable of binding to one or more antigens, e.g., specifically binding to one or more antigens and at least comprising a CDR1. In one example, the heavy chain comprises three or four FRs (e.g., FR1, FR2, FR3 and optionally FR4) together with three CDRs. For example, a heavy chain comprises FRs and CDRs positioned as follows residues 1-25 or 1-30 (FR1), 31-35 (or 35b) (CDR1), 36-49 (FR2), 50-65 (CDR2), 66-94 (FR3), 95-102 (CDR3) and 103-113 (FR4), numbered according to the Kabat numbering system. In one example, the heavy chain is derived from an immunoglobulin comprising said heavy chain and a plurality of (e.g., 3 or 4) constant domains or linked to a constant fragment (Fc).

As used herein, the term "light chain variable region" or "$V_L$" shall be taken to mean a protein capable of binding to one or more antigens, e.g., specifically binding to one or more antigens and at least comprising a CDR1. For example, the light chain comprises three or four FRs (e.g., FR1, FR2, FR3 and optionally FR4) together with three CDRs. For example, a light chain comprises FRs and CDRs positioned as follows residues 1-23 (FR1), 24-34 (CDR1), 35-49 (FR2), 50-56 (CDR2), 57-88 (FR3), 89-97 (CDR3) and 98-107 (FR4), numbered according to the Kabat numbering system. In one example, the light chain is derived from an immunoglobulin comprising said light chain linked to one constant domain and/or not linked to a constant fragment (Fc).

The term "functional fusion protein" shall be understood to mean that each component polypeptide of the fusion protein is expressed in its correct reading frame and folds correctly. For example, a functional fusion protein comprising a $V_H$ and antibody heavy chain constant regions is an antibody heavy chain.

Polypeptides/Multimeric Proteins

The present disclosure contemplates production of expression vectors comprising nucleic acids encoding any polypeptide. Exemplary polypeptides comprise antibody variable domains, e.g., are antibodies, e.g., comprising light chains and heavy chains.

Production/Isolation of Antibodies
Immunization-Based Methods

To generate antibodies, an antigen or nucleic acid encoding same, optionally formulated with any suitable or desired carrier, adjuvant, or pharmaceutically acceptable carrier, is conveniently administered to a subject (e.g., a non-human subject, such as, a mouse, a rats, a chicken etc) in the form of an injectable composition. Injection may be intranasal, intramuscular, sub-cutaneous, intravenous, intradermal, intraperitoneal, or by other known route. Optionally, the antigen or nucleic acid encoding same is administered numerous times. Means for preparing and characterizing antibodies are known in the art. (See, e.g., Antibodies: A Laboratory Manual, Cold Spring Harbor Laboratory, 1988).

Monoclonal antibodies are exemplary antibodies. Generally, such antibodies are produced using a method involving, immunizing a subject (e.g., a rodent, i.e., mouse or rat) with the cytokine or nucleic acid encoding same under conditions sufficient to stimulate antibody producing cells. Alternatively, a mouse genetically-engineered to express human immunoglobulin proteins, and not to express murine immunoglobulin proteins, is immunized to produce an antibody (e.g., as described in PCT/US2007/008231 and/or Lonberg et al., *Nature* 368 (1994): 856-859). Following immunization, antibody producing somatic cells (e.g., B lymphocytes) are fused with immortal myeloma cells. Various methods for producing such fused cells (hybridomas) are known in the art and described, for example, in Kohler and Milstein, *Nature* 256, 495-497, 1975. The hybridoma cells can then be cultured under conditions sufficient for antibody production.

The present disclosure contemplates other methods for producing antibodies, e.g., ABL-MYC technology (as described, for example in Largaespada et al, *Curr. Top. Microbiol. Immunol*, 166, 91-96. 1990).

Following production of antibodies in an animal nucleic acid encoding the variable regions can be cloned using methods known in the art and/or described herein and cloned using a method of the disclosure. The methods of the present disclosure are useful for cloning nucleic acids encoding large numbers of antibodies. In the case of non-human antibodies, the can be used to produce chimeric antibodies. In the case of human antibodies, the methods of the present disclosure are useful for cloning to produce a different isotype and/or to simplify cloning, e.g., since it is only necessary to clone variable region encoding sequences as opposed to the entire antibody.

Library-Based Methods

The present disclosure also encompasses screening of libraries of antibodies or fragments thereof.

Examples of this disclosure include naïve libraries (from unchallenged subjects), immunized libraries (from subjects immunized with an antigen) or synthetic libraries. Nucleic acid encoding antibodies or regions thereof (e.g., variable domains) are cloned by conventional techniques (e.g., as disclosed in Sambrook and Russell, eds, Molecular Cloning: A Laboratory Manual, 3rd Ed, vols. 1-3, Cold Spring Harbor Laboratory Press, 2001) and used to encode and display proteins using a method known in the art. Other techniques for producing libraries of proteins are described in, for example in U.S. Pat. No. 6,300,064 (e.g., a HuCAL library of Morphosys AG); U.S. Pat. Nos. 5,885,793; 6,204,023; 6,291,158; or U.S. Pat. No. 6,248,516.

The antibodies or fragments thereof (e.g., scFv or Fab fragments) may be soluble secreted proteins or may be presented as a fusion protein on the surface of a cell, or particle (e.g., a phage or other virus, a ribosome or a spore). Various display library formats are known in the art. For example, the library is an in vitro display library (e.g., a ribosome display library, a covalent display library or a mRNA display library, e.g., as described in U.S. Pat. No. 7,270,969). In yet another example, the display library is a phage display library wherein proteins comprising antigen binding domains of antibodies are expressed on phage, e.g., as described in U.S. Pat. Nos. 6,300,064; 5,885,793; 6,204, 023; 6,291,158; or U.S. Pat. No. 6,248,516. Other phage display methods are known in the art and are contemplated by the present disclosure. Similarly, methods of cell display are contemplated by the disclosure; e.g., bacterial display libraries, e.g., as described in U.S. Pat. No. 5,516,637; yeast display libraries, e.g., as described in U.S. Pat. No. 6,423, 538 or a mammalian display library.

Methods for screening display libraries are known in the art. In one example, a display library of the present disclosure is screened using affinity purification, e.g., as described in Scopes (In: Protein purification: principles and practice, Third Edition, Springer Verlag, 1994). Methods of affinity purification typically involve contacting proteins comprising antigen binding domains of antibodies displayed by the library with a target antigen and, following washing, eluting those domains that remain bound to the antigen.

Any variable regions or scFvs identified by screening are readily modified into a complete antibody, e.g., using a method of the present disclosure.

Recombinant Antibodies

The present disclosure is also useful for cloning to produce chimeric, de-immunized, humanized or human antibodies.

The term "humanized antibody" shall be understood to refer to a protein comprising a human-like variable region in which the antigen binding site is derived from an antibody from a non-human species and the remaining antibody structure is based upon the structure and/or sequence of a human antibody. The antigen-binding site comprises residues from complementarity determining regions (CDRs) from the non-human antibody grafted onto appropriate framework regions (FRs) from a human antibody (this form of protein is also called a CDR grafted antibody). Any additional regions of the protein (e.g., Fc region) are human or derived from a human protein. Humanized antibodies also include antibodies in which the antigen binding site is modified by one or more amino acid substitutions and/or FR residues of the human protein are replaced by corresponding non-human residues. Humanized antibodies may also comprise residues which are found neither in the human antibody or in the non-human antigen binding site. In general, the humanized antibodies will comprise substantially all of at least one, and typically two (preferably, three), CDRs, in which all or substantially all of the CDR regions correspond to those of a non-human antibody and all or substantially all of the FR regions are those of a human antibody. Humanization can be performed using a method known in the art, e.g., U.S. Pat. Nos. 5,225,539, 6,054,297, or U.S. Pat. No. 5,585,089.

The term "human antibody" as used herein refers to antibodies having variable and, optionally, constant antibody regions derived from or corresponding to sequences found in humans, e.g. in the human germline or somatic cells. The "human" antibodies can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein. These "human antibodies" do not actually need to be produced by a human, rather, they can be produced using recombinant means and/or isolated from a transgenic animal (e.g., a mouse) comprising nucleic acid encoding human antibody constant and/or variable regions and/or by phage display (as described above) and or using guided selection (e.g., as described in or U.S. Pat. No. 5,565,332). This term also encompasses affinity matured forms of such antibodies.

The term "chimeric antibody" refers to an antibody in which a $V_H$ or $V_L$ is identical with or homologous to corresponding sequences in proteins derived from a particular species (e.g., murine, such as mouse or rat) or belonging to a particular antibody class or subclass, while the remainder of the chain(s) is identical with or homologous to corresponding sequences in proteins derived from another species (e.g., primate, such as human) or belonging to another antibody class or subclass. The production of such chimeric antibodies is known in the art, and may be achieved by standard means (as described, e.g., in U.S. Pat. Nos. 5,807,715; 4,816,567 and U.S. Pat. No. 4,816,397).

The present disclosure also contemplates a deimmunized antibodies, e.g., as described in WO00/34317 and WO2004/108158.

Other Antibody Variable Domain Containing Polypeptides/Multimeric Proteins

Single-Domain Antibodies

In some examples, an antibody variable domain polypeptide is a single-domain antibody (which is used interchangeably with the term "domain antibody" or "dAb"). A single-domain antibody is a single polypeptide chain comprising all or a portion of a $V_H$ or $V_L$. Exemplary disclosures of single domain antibodies include U.S. Pat. No. 6,248,516 or WO90/05144

Diabodies, Triabodies, Tetrabodies

Exemplary multimeric proteins comprising a variable domain containing polypeptide are diabodies, triabodies, tetrabodies and higher order protein complexes such as those described in WO98/044001 and WO94/007921.

Essentially a diabody is a multimeric protein comprising two associated polypeptides, each polypeptide comprising the structure $V_L$-X-$V_H$ or $V_H$-X-$V_L$, wherein X is a linker comprising insufficient residues to permit the $V_H$ and $V_L$ in a single polypeptide to associate or is absent, and wherein the $V_H$ of one polypeptide binds to a $V_L$ of the other chain to form an antigen binding site, i.e., to form a Fv capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

A triabody is a trimeric form of a diabody and a tetrabody is a tetrameric form of a diabody.

Single Chain Fv (scFv)

The skilled artisan will be aware that scFvs are a polypeptide comprising two antibody variable regions, which comprise $V_H$ and $V_L$ regions in a single polypeptide. For example, the polypeptide comprises a polypeptide linker between the $V_H$ and $V_L$ which enables the scFv to form a Fv. This is distinct from a diabody or higher order multimer in which variable regions from different polypeptide chains associate or bind to one another. For example, the linker comprises in excess of 12 amino acid residues with $(Gly_4Ser)_3$ being one of the more favored linkers for a scFv. For a review of scFv, see Plückthun in The Pharmacology of Monoclonal Antibodies, vol. 113, Rosenburg and Moore eds., Springer Verlag, New York, pp. 269-315, 1994.

Minibodies

The skilled artisan will be aware that a minibody comprises the $V_H$ and $V_L$ domains of an antibody fused to the $C_H2$ and/or $C_H3$ domain of an antibody. Optionally, the minibody comprises a hinge region between the $V_H$ and a $V_L$ and the $C_H2$ and/or $C_H3$ domains, sometimes this conformation is referred to as a Flex Minibody. Exemplary minibodies and methods for their production are described, for example, in WO94/09817.

Antibody Fragments

Other polypeptides comprising antibody variable domains or multimeric proteins comprising same are antibody fragments. While these polypeptides/proteins are termed fragments, this does not mean that they are derived directly from an antibody, since they can be produced by recombinant means. Exemplary fragments are Fab fragments, $F(ab)_2$ fragments and $Fab_2$ fragments. A "Fab fragment" consists of a polypeptide having a $V_H$-$C_H1$ and a polypeptide having $V_L$-$C_L$. An "F(ab')$_2$ fragment" of an antibody consists of a dimer of two Fab each additionally comprising a hinge region, the dimer held together by two disulfide bonds. An "Fab$_2$" fragment is a recombinant fragment comprising two Fab fragments linked using, for example a leucine zipper or a $C_H3$ domain.

Other Polypeptides/Multimeric Proteins

As will be apparent to the skilled artisan from the description herein, the present disclosure is useful for producing expression constructs for expressing any polypeptide or multimeric protein. Exemplary polypeptides and/or proteins are described herein.

One exemplary form of a polypeptide is a Fc fusion polypeptide. In this regard, the present disclosure is amenable to high throughput re-formatting of mutant version of such proteins. For example, a series of mutants can be screened for a desirable property, and those having that property are cloned using a method described herein to produce a Fc fusion. By way of example only, mutants of interleukin-2 (IL-2) are screened to identify those that bind to low affinity IL-2 receptors but not CD25 containing receptors. Any mutants having this property are then cloned using a method described herein to produce a Fc fusion protein. This protein is then tested for its ability to treat cancer without causing vascular leakage syndrome.

The present disclosure is also useful for producing an expression construct for expressing a polypeptide of interest and a polypeptide required for correct folding and/or production, e.g., a chaperone, a polypeptide of interest is expressed with a polypeptide required for activation, e.g., a protease.

Additional multimeric proteins contemplated by the disclosure are, for example, multi-specific Fc fusion proteins. For example, the first nucleic acid encodes a Fc fusion protein comprising a first polypeptide and the second nucleic acid encodes a Fc fusion protein a second polypeptide. Obviously, the first and second nucleic acids can encode only the polypeptides and an expression vector and the nucleic acid encoding the selectable marker can comprise regions encoding the Fc regions. Exemplary polypeptides that can be produced as Fc fusions include, a tumor necrosis factor receptor, erythropoietin, an interleukin (e.g., interleukin 2), an interleukin receptor (e.g., interleukin-1 receptor or interleukin 2 receptor) or CTLA4.

Another multimeric protein contemplated by the present disclosure is a multi-specific minibody. In accordance with the present disclosure, the first nucleic acid encodes a scFv that binds a first antigen and the second nucleic acid encodes a scFv that binds a second antigen. The $C_H2/C_H3$ containing region can be encoded by a nucleic acid in the first or second nucleic acid or can be encoded by regions of an expression vector and the nucleic acid encoding the selectable marker.

Another multimeric protein contemplated by the present disclosure is a multispecific diabody, triabody or tetrabody. The present disclosure is amenable for producing multispecific diabodies in which one Fv is constant, e.g., always binds to a set antigen, e.g., a T cell antigen such as CD4. The nucleic acid encoding this Fv and the linker region can be included in an expression vector and the nucleic acid encoding the selectable marker. The nucleic acids encoding the $V_H$ and $V_L$ of the other Fv can then be cloned using a method of the disclosure.

A further multimeric protein contemplated by the present disclosure is a multimeric cytokine, e.g., interleukin 23 or interleukin 12. The skilled artisan will be aware that numerous cytokines share common subunits, and the present disclosure provides a suitable means for cloning various combinations of different subunits to produce known or new multimeric cytokines.

Expression Constructs

As will be apparent to the skilled artisan from the description herein, the present disclosure is useful for producing expression constructs, i.e., in which nucleic acids are operably linked to suitable promoters.

Cell free expression systems are contemplated by the present disclosure. For example, a nucleic acid is operably linked to a suitable promoter, e.g., a T7 promoter, and the resulting expression construct exposed to conditions sufficient for transcription and translation. Typical expression vectors for in vitro expression or cell-free expression have been described and include, but are not limited to the TNT T7 and TNT T3 systems (Promega), the pEXP1-DEST and pEXP2-DEST vectors (Invitrogen).

Many vectors for expression in cells are available. The vector components generally include, but are not limited to, one or more of the following: a signal sequence, a sequences encoding a polypeptide(s), an enhancer element, a promoter, and a transcription termination sequence. The skilled artisan will be aware of suitable sequences for expression of a protein. For example, exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters include those active in prokaryotes (e.g., phoA promoter, β-lactamase and lactose promoter systems, alkaline phosphatase, a tryptophan (trp) promoter system, and hybrid promoters such as the tac promoter). These promoter are useful for expression in prokaryotes including eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*. In one example, the host is *E. coli*. One preferred *E. coli* cloning host is *E. coli* 294 (ATCC 31,446), although other strains such as *E. coli* B, *E. coli* X 1776 (ATCC 31,537), and *E. coli* W3110 (ATCC 27,325), DH5a or DH10B are suitable.

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEE1 promoter.

Typical promoters suitable for expression in insect cells include, but are not limited to, the OPEI2 promoter, the insect actin promoter isolated from *Bombyx muni*, the *Drosophila* sp. dsh promoter and the inducible metallothionein promoter. Exemplary insect cells for expression of recombinant proteins include an insect cell selected from the group comprising, BT1-TN-5B1-4 cells, and *Spodoptera frugiperda* cells (e.g., sf19 cells, sf21 cells). Suitable insects for the expression of the nucleic acid fragments include but are not limited to *Drosophila* sp. The use of *S. frugiperda* is also contemplated.

Marker Proteins

Suitable marker proteins for the present disclosure include those that confer antibiotic resistance or resistance to another toxic compound. Examples of marker proteins conferring resistance to antibiotics include neomycin phosphtransferase that phosphorylates neomycin and kanamycin, or hpt, phosphorylating hygromycin, or proteins conferring resistance to, for example, bleomycin, streptomycin, tetracycline, chloramphenicol, ampicillin, gentamycin, geneticin (G418), spectinomycin or blasticidin). In one example, the protein confers resistance to chloramphenicol. For example, the protein is a gene from *E. coli* designated CmR, e.g., as described in Nilsen et al., *J. Bacteriol.*, 178: 3188-3193, 1996.

Alternatively, the marker protein complements an auxotrophy in a cell. For example, a eukaryotic cell lacking HPRT expression is transformed with an expression construct comprising a nucleic acid encoding HPRT. Expression of the reporter gene results in the cell being capable of growing in HAT medium, while cells that do not express the reporter gene are not capable of growing in these conditions.

Alternatively, in the case of a yeast cell, the marker protein is, for example, LEU2 or LYS2 or TRP. Such a reporter gene is capable of complementing a yeast cell that is auxotrophic for the relevant gene, and, as a consequence unable to produce the relevant amino acid.

In another example, the marker protein that is directly detectable, e.g., is a fluorescent protein. Several fluorescent reporter genes are known in the art and include, for example, those that encode green fluorescent protein (GFP), enhanced green fluorescent protein (eGFP), red shifted green fluorescent protein (RFP), cyan fluorescent protein (CFP), yellow fluorescent protein (YFP), monomeric discosoma red fluorescent protein (dsRED), or dsRED2; monomeric orange fluorescent protein or monomeric GFP from *Aequorea coerulescens*. These proteins permit selection of a cell expressing the marker protein using standard techniques, e.g., fluorescence activated cell sorting (FACS).

In a further example, a marker gene is an enzyme that catalyzes a detectable reaction. Exemplary enzymatic reporter genes include for example, β-galactosidase, alkaline phosphatase, firefly luciferase or *Renilla* luciferase. For example, the expression of β-galactosidase is detected by the addition of the substrate 5-bromo-4-chloro-3-indolyl-beta-D-galactopyranoside (x-gal), which is hydrolyzed by β-galactosidase to produce a blue colored precipitate. Alternatively, the expression of either firefly luciferase or *Renilla* luciferase is detected by addition of a substrate that in the presence of the relevant protein is luminescent and is detectable, for example, using a spectrophotometer.

Cloning

Nucleic acid encoding polypeptide(s) can be isolated or produced using any method known in the art, e.g., as described in Sambrook et al. Molecular Cloning: A Laboratory Manual, Cold Spring Harbour Laboratory Press, 1989 and/or Ausubel et al. (editors), Current Protocols in Molecular Biology, Greene Pub. Associates and Wiley-Interscience (1988, including all updates until present).

For example, nucleic acid encoding the polypeptides is produced using polymerase chain reaction (PCR). Methods for performing PCR are known in the art. In the case of antibodies, PCR can be used to amplify variable regions, optionally linked to one or more constant regions, e.g., form a subject or from a library or after screening a library. Primers for such amplifying nucleic acids encoding antibody regions are known in the art (e.g., as described in U.S. Pat. No. 6,096,551 and WO00/70023). In a further example, nucleic acid can be produced/isolated using restriction endonuclease digestion according to standard methods in the art.

Methods for linking nucleic acids will be apparent to the skilled artisan and described, for example, in Sambrook et al. Molecular Cloning: A Laboratory Manual, Cold Spring Harbour Laboratory Press, 1989 and/or Ausubel et al. (editors), Current Protocols in Molecular Biology, Greene Pub. Associates and Wiley-Interscience (1988, including all updates until present). In one example, the method makes use of a ligase, e.g., T4 DNA ligase, to link nucleic acids.

In one exemplary form of the disclosure, ligase independent cloning is used to link nucleic acids.

In one form of ligase independent cloning, complementary single stranded regions are included in two nucleic acids to be linked. These nucleic acids are then hybridized to one another and the resulting nucleic acid is transformed into a cell, in which endogenous enzymes repair any remaining gap and form a single contiguous nucleic acid.

In another form of ligase independent cloning, one or more enzymes are used to enhance formation of a single nucleic acid molecule. For example, U.S. Pat. No. 7,575,860 describes a technique in which a polymerase having 3'-5' endonuclease activity (e.g., from Vaccinia virus) is used to link the two nucleic acids. For example, the nucleic acids to be linked comprise regions that are substantially identical or are identical. These regions can be between 5 to 50 nucleotides in length, e.g., about 12 to 15 nucleotides in length, such as about 15 nucleotides in length. The nucleic acids to be linked are then contacted with a polymerase having 3'-5' exonuclease activity. Exemplary polymerases include vaccinia DNA polymerase, T4 DNA polymerase and the Klenow fragment of *E. Coli* DNA polymerase I. In one example, the nucleic acid is additionally contacted with a single strand DNA binding protein, such as, vaccinia and *E. coli* single strand binding proteins, Herpes simplex virus ICP8 protein, and yeast and human replication Protein A (eg. yRPA and hRPA). Kits for performing this type of ligase independent cloning are commercially available from Clontech under the trademark In-Fusion®.

Additional ligase independent cloning methods are known in the art and include, for example, ligation independent cloning (LIC; e.g., as described in Aslanidis et al., *Nucl. Acids Res.*, 18: 6069), T7 exonuclease-mediated cloning (U.S. Pat. No. 5,580,759), hetero-stagger PCR-based cloning (Liu et al., *Nucleic Acids Res* 24: 2458-2459, 1996), uracil-excision based cloning (Nisson et al., *PCR Meth. Appl.* 1:120-123, 1991), phosphorothioate-based ligase-independent cloning (e.g., as described by Blanusa et al., *Anal. Biochem*, 406: 141-146, 2010).

The resulting nucleic acid can then be introduced into cells using a standard method in the art, e.g., as discussed below.

In one example, recombination is used to link nucleic acids. For example, two nucleic acids to be linked both comprise a region (e.g., 100 nucleotides or 50 nucleotides or 20 nucleotides or 10 nucleotides in length) that are identical or substantially identical. The nucleic acids are then introduced into cells capable of homologous recombination and cells in which homologous recombination has occurred are selected, e.g., by selecting for expression of the marker protein.

Reformatting of Antibodies

The method of the present disclosure is suited for reformatting antibodies. As used herein, the term "reformatting antibodies" shall be understood to mean producing a protein comprising a $V_L$ fused to a $C_L$ and a $V_H$ fused to a heavy chain constant regions, such as a $C_H1$ region and Fc region. At least the $V_L$ and $V_H$ and, optionally the $C_L$ and/or $C_H1$ may be derived from a clone from a library, e.g., a phage display library or may be derived from a complete antibody, e.g., if the antibody reformatting is being used to produce a chimeric antibody or to change antibody subtype/isotype.

In one example, a method for reformatting an antibody comprises linking the following unlinked nucleic acids:
(i) a first nucleic acid encoding an antibody light chain variable region and a light chain constant region;
(ii) a nucleic acid encoding a marker protein that facilitates detection and/or isolation of a cells expressing the marker protein and a first promoter;
(iii) a second nucleic acid encoding an antibody heavy chain variable region; and
(iv) an expression vector comprising a second promoter and a sequence encoding one or more antibody heavy chain constant regions; wherein the vector does not comprise a nucleic acid encoding the marker protein encoded by the nucleic acid at (ii) such that:
(a) the second promoter and first nucleic acid are operably linked;
(b) the nucleic acid encoding the marker protein is positioned between the first and second nucleic acids such that the first promoter is operably linked to the second nucleic acid;
(c) the second nucleic acid and the sequence encoding one or more antibody heavy chain constant regions are linked so as to encode a functional fusion protein.

In one example, the expression vector comprises a nucleic acid encoding a secretion signal operably linked to the second promoter, positioned such that the nucleic acid encoding the secretion signal becomes operably linked to the first nucleic acid (e.g., at the 5' end of the first nucleic acid).

In one example, the nucleic acid encoding a marker protein additionally comprises a polyadenylation signal, positioned such that the polyadenylation signal becomes operably linked to the first nucleic acid (e.g., at the 3' end of the first nucleic acid).

In one example, the nucleic acid encoding a marker protein additionally comprises a promoter, positioned such that it becomes operably linked to the second nucleic acid (e.g., at the 5' end of the second nucleic acid).

In another example, the nucleic acid encoding a marker protein additionally comprises a secretion signal, positioned such that it becomes operably linked to the second nucleic acid (e.g., at the 5' end of the second nucleic acid). The secretion signal can be positioned 3' to the promoter described in the previous paragraph.

In a still further example, the first nucleic acid does not encode a light chain constant region, and a light chain constant region encoding nucleic acid is included in the nucleic acid encoding a marker protein, positioned such that it becomes linked to the $V_L$ to form a functional fusion protein. The light chain constant region can be positioned 5' to the polyadenylation signal discussed above.

In one example, the nucleic acids are linked using ligase independent cloning, e.g., as described herein.

In one example, following linking the nucleic acids, the expression construct is introduced into a cell, e.g., a bacterial cell, such as an *E. coli* cell. Cells expressing the marker protein can then be selected.

In one example, each of the previously recited steps is performed in solution. For example, the steps are not performed on a solid medium, e.g., cells are not plated onto solid medium.

In one example, the expression construct is isolated and/or purified from the cell and introduced into another cell (e.g., a mammalian cell) for expression of the encoded polypeptide(s)/multimeric protein.

The present disclosure also encompasses the vector produced by a method described herein. For example, the present disclosure encompasses a vector for expressing an antibody, the vector comprising the following components:
(i) a first promoter operably linked to a nucleic acid encoding a polypeptide comprising an antibody light chain variable region and an antibody light chain constant region;
(ii) a nucleic acid encoding a marker protein that facilitates detection and/or isolation of a cells expressing the marker protein; and
(iii) a second promoter operably linked to a nucleic acid encoding a polypeptide comprising an antibody heavy variable region and one or more antibody heavy chain constant regions,
wherein the nucleic acid encoding the marker protein is positioned between the first nucleic acid and the second promoter.

In one example, the vector comprises the following components:
(i) a nucleic acid capable of expressing an antibody light chain comprising:
 a) a promoter;
 b) a signal sequence;
 c) a nucleic acid encoding a $V_L$ and $C_L$; and
 d) a polyadenylation signal;
(ii) a nucleic acid encoding a marker protein that facilitates detection and/or isolation of a cells expressing the marker protein; and
(iii) a nucleic acid capable of expressing an antibody heavy chain comprising:
 a) a promoter;
 b) a signal sequence;
 c) a nucleic acid encoding a $V_H$, a $C_H1$ and a Fc region; and
 d) a polyadenylation signal
wherein the nucleic acid encoding the marker protein is positioned between the first nucleic acid and the second nucleic acid.

Cells/Expression

Following production of an expression construct, the construct can be introduced into a suitable cell for expression. Exemplary cells are known in the art and/or described herein.

Means for introducing the isolated nucleic acid or an expression construct comprising same into a cell for expression are known to those skilled in the art. The technique used for a given cell depends on the known successful techniques. Methods for introducing nucleic acid into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein of this disclosure may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Isolation of Proteins

A polypeptide/multimeric protein produced as described herein can be isolated. By "isolated" is meant that the protein is substantially purified or is removed from its naturally-occurring environment, e.g., is in a heterologous environment. By "substantially purified" is meant the protein is substantially free of contaminating agents, e.g., at least about 70% or 75% or 80% or 85% or 90% or 95% or 96% or 97% or 98% or 99% free of contaminating agents.

Methods for purifying a protein of the disclosure are known in the art and/or described herein.

When using recombinant techniques, the protein of the disclosure can be produced intracellularly, in the periplasmic space, or directly secreted into the medium. If the protein is produced intracellularly, as a first step, the particulate debris, either host cells or lysed fragments, is removed, for example, by centrifugation or ultrafiltration. Where the protein is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein prepared from the cells can be purified using, for example, hydroxyl apatite chromatography, gel electrophoresis, dialysis, and affinity chromatography, with affinity chromatography being an exemplary purification technique. The suitability of protein A as an affinity ligand depends on the species and isotype of any immunoglobulin Fc domain that is present in the protein (if present at all). Protein A can be used to purify immunoglobulins that are based on human γ1, γ2, or γ4 heavy chains. Protein G is recommended for all mouse isotypes and for human γ3. Otherwise affinity purification can be performed using the antigen or epitopic determinant to which a variable region in a protein of the disclosure binds or was raised. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the protein to be recovered.

The skilled artisan will also be aware that a polypeptide/multimeric protein can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. For example a hexa-his tag containing protein is purified using methods known in the art, such as, by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Following any preliminary purification step(s), the mixture comprising the protein of the disclosure and contaminants may be subjected to low pH hydrophobic interaction chromatography.

High Throughput Methods

As discussed herein, the method of the disclosure is amenable to high-throughput production of expression constructs and/or cells comprising same.

In one example, such a high throughput method comprises performing a method of the disclosure a plurality of times in parallel. For example, in a plate comprising a plurality of wells each well contains a reaction in which the requisite nucleic acids are linked. These nucleic acids are then transformed into a cell and the cells selected in solution. Optionally, the cells are then expanded and the expression construct isolated such that it is ready for transfection into another cell, e.g., a mammalian cell.

In one example, the method comprises performing a method of the present disclosure in each of a plurality of wells in a plate to thereby produce an expression construct; transferring the expression construct to a plate comprising cells to be transformed, transforming the cells and selecting cells comprising an expression vector.

Optionally, the method additionally comprises expanding the selected cells and isolating the expression construct therefrom.

In one example, this method or parts thereof is(are) performed using a robotic system.

Kits

The present disclosure also provides a kit for producing an expression vector for expressing a polypeptide/multimeric protein, the kit comprising:
(i) an expression vector;
(ii) a nucleic acid encoding a marker protein that facilitates detection and/or isolation of a cells expressing the marker protein; and
(iii) instructions for use in a method or process described herein.

In one example, the nucleic acid encoding the marker protein is in the form of a vector and the kit comprises instructions to isolate the nucleic acid, e.g., using restriction endonuclease digestion or nucleic acid amplification.

In one example, the kit additionally comprises reagents for ligase independent cloning.

In another example, the kit comprises a ligase.

In another example, the kit comprises primers for amplifying polypeptide(s), e.g., primers for amplifying a $V_H$ and/or a $V_L$ or a $V_L$ and $C_L$.

The present disclosure also includes the following non-limiting examples.

EXAMPLE 1

Insert Tagged Positive Selection (INTAPS) Adaptors

With classical selection using a selection marker (e.g. AmpR) located on the vector backbone, the uncut or re-ligated parental plasmid will be selected along with the recombinant plasmid, thus generating the cloning background. This problem led to the inventors developing INTAPS cloning in which a positive selection marker (e.g. CmR) is co-inserted into the plasmid during the cloning process, hence permitting selection against any uncut or re-ligated parental plasmid and reducing or eliminating cloning background (as shown in FIG. 1)

Figure 2:
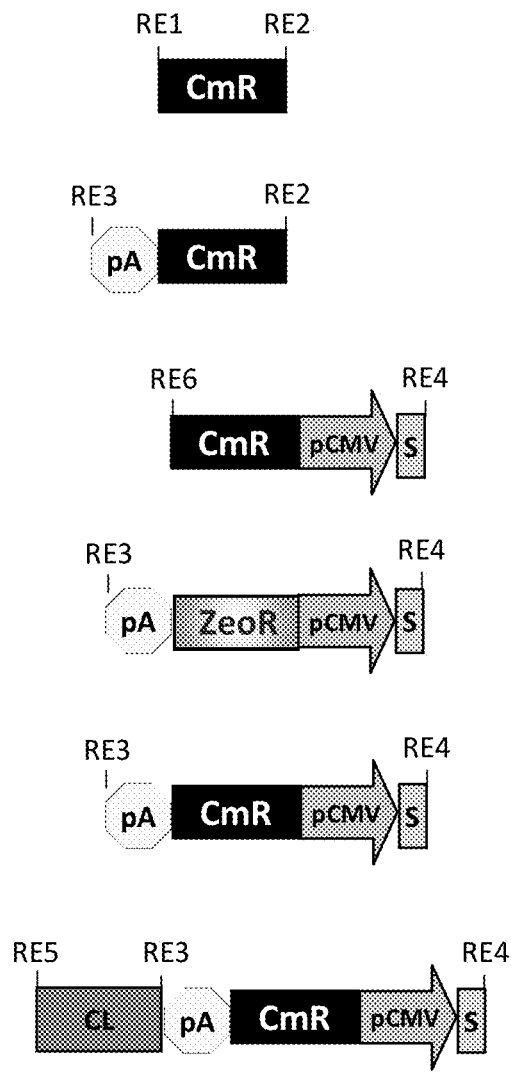
FIG. 2 is a graphical representation depicting examples of INTAPS adaptors. The adaptors can simply be a positive selection marker gene such as CmR (conferring chloramphenicol resistance) or ZeoR (conferring Zeocin resistance). They can also be joined with certain nucleic acid sequences useful in the functionality of the final expression construct(s) to be made, e.g., a polyadenylation signal (pA), a promoter (e.g., a CMV immediate early promoter, pCMV), a secretion signal (S) and/or a light chain constant region (CL). "RE" depict positioning of optional restriction endonuclease cleavage sites.

In the context of the present example, an INTAPS adaptor is a DNA fragment containing a positive selection marker gene and, optionally, other sequence elements (eg, BGHpA, CMV promoter). FIG. 2 illustrates a number of exemplary INTAPS adaptors generated and used for vector construction.

The BGHpA-CmR-CMVpro adaptor was generated using Splicing by Overlap Extension (SOE) PCR. The BGH pA was PCR amplifed using primers BGHpAf and BGH/cmRf (Table 1) from pcDNA3.1. The CmR marker gene was PCR amplified using BGH/cmRr and CmR/CMVr from the Gateway vector conversion system (Invitrogen). The CMV promoter region was PCR amplified from pcDNA3.1 using primers CmR/CMVf and CMV/SPr. The signal peptide was amplified from an in-house antibody contruct using CMV/SPf and VHspR primers. The four DNA fragments were joined together by SOE-PCR and then subcloned into pCR4Blunt-TOPO vector (Invitrogen) according to the manufacturer's instructions.

TABLE 1

Primer sequences for INTAPS adaptors generation

| Name | Sequence | SEQ ID NO |
|---|---|---|
| BGHpAf: | AAAGGCGCGCCTCGACTGTGCCTTCTAG | 1 |
| BGH/CmRF | GATGCGGTGGGCTCTATGGCTGAACGAGAAACGTAAAA | 2 |
| BGH/CmRr: | TTTTACGTTTCTCGTTCAGCCATAGAGCCCACCGCATC | 3 |
| CmR/CMVf: | TGGCAGGGCGGGGCGTAAGTTGACATTGATTATTGAC | 4 |
| CmR/CMVr: | GTCAATAATCAATGTCAACTTACGCCCCGCCCTGCCA | 5 |
| CMV/SPf: | TACGACTCACTATAGGGCCGCCACCATGGGATGGAGCTG | 6 |
| CMV/SPr: | CAGCTCCATCCCATGGTGGCGGCCCTATAGTGAGTCGTA | 7 |
| VHspR: | GCTGTGCACTCCAGTAGCTG | 8 |
| BGH/ZeoRF | GATGCGGTGGGCTCTATGGGCCTGATGCGGTATTTTC | 9 |
| BGH/ZeoRr: | GAGAAAATACCGCATCAGGCCATAGAGCCCACCGCA | 10 |
| ZeoR/CMVf: | GCCGAGGAGCAGGACTGACGTTGACATTGATTATTG | 11 |
| ZeoR/CMVr: | TGGCAGGGCGGGGCGTAAGTTGACATTGATTATTGA | 12 |

The BGHpA-ZeoR-CMVpro adaptor was similarity generated by SOE-PCR using the Zeocin resistance marker gene, PCR amplified from pcDNA3.1zeo vector (Invitrogen). Other adaptors depicted in FIG. 2 were generated from the above two adaptors by restriction digestion or PCR.

EXAMPLE 2

Comparison Between Classical Cloning and INTAPS Cloning Methods

Figure 3:
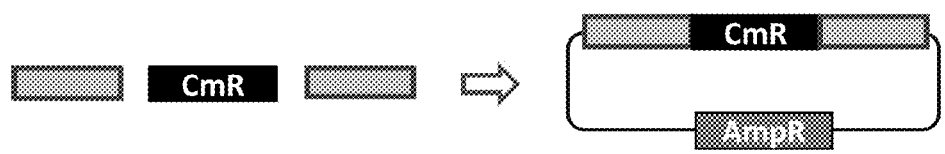
FIG. 3 Panel A depicts three inserts cloned into a vector containing the AmpR marker. One of the insert contains a CmR selection marker (INTAPS adaptor) which is different to the marker gene located in the vector. The transformed cells were plated onto agar plates containing either chloramphenicol (INTAPS selection) or ampicillin (classical selection).

To demonstrate the efficacy of INTAPS selection in reducing or eliminating cloning background resulting from uncut or re-ligated parental vector, two independent DNA fragments were co-inserted with an INTAPS adaptor, encoding the CmR marker, into a plasmid vector by using T4 DNA ligase (as depicted in FIG. 3 Panel A). Cut vector DNA (in the absence of insert) was also transformed into Top10 cells as a negative control to monitor the cloning background. The ligation mix was transformed into Top10 competent cells (Invitrogen). Following incubation on ice for 30 min, the cells were heated-shocked at 42° C. for 45 sec. SOC medium (500 µl) was added to the cells followed by incubation at 37° C. for 1 hour. The cells were then pelleted and plated onto petri dishes containing medium comprising 100 µg/ml ampicillin or 34 µg/ml chloramphenicol.

The number of colonies on each plate were counted and the results are shown in FIG. 3 Panel B. The negative control with cut vector only gave over 1000 colonies on the ampicillin containing plate (classical selection), which represents the cloning background. In contrast, the same ligation mix gave no colonies when selected on the choramphenicol plate (INTAPS selection), indicating the elimination of the cloning background. The ligation with three inserts gave 753 colonies on the amphicillin containing plate and 168 colonies on chloramphenicol containing plate.

Colonies (2-7) were picked from each plate and plasmid DNA was isolated using QIAprep Spin Miniprep kit (QIAGEN). The DNA was digested with appropriate restriction enzymes and analysed on 1% agarose gels. The two colonies from the negative control plate contained no insert as expected. Only 3 out of the 7 colonies from the ampicillin plate (classical selection) contained the correct inserts. In contrast, all the 7 clones from the chloramphenicol plate (INTAPS selection) contained the correct inserts.

These data indicate that INTAPS reduces or eliminates cloning background due to uncut or re-ligated parental vector.

EXAMPLE 3

Cloning of Two Inserts by INTAPS Cloning

Figure 4:
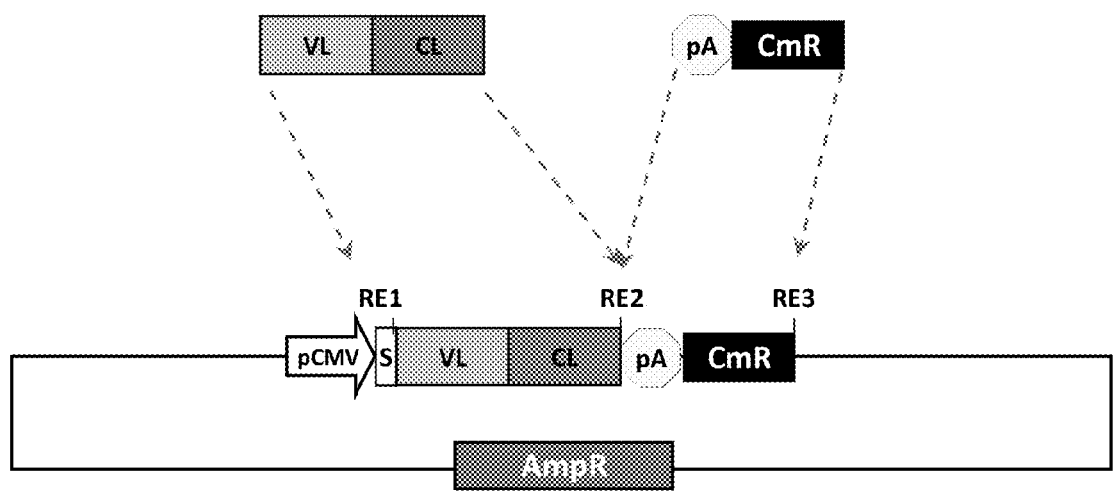
FIG. 4 is a graphical representation showing cloning of two inserts cloned into a single vector using INTAPS cloning. The two inserts are ligated into the vector by T4 DNA ligase and the recombinant plasmids selected with chloramphenicol. Abbreviations used in this drawing are described above.

Two DNA fragments, one of which contains an INTAPS selection adaptor were digested with appropriate restriction enzymes. They were ligated using T4 DNA ligase into a linearized vector. The ligation mix was transformed into *E.* coli cells and selected in liquid media containing chloramphenicol. Plasmid DNA was isolated and analyzed by restriction endonuclease digestion, which confirmed the correct construct. An example of the application of this cloning method is depicted in FIG. 4.

EXAMPLE 4

Cloning of Three Inserts by INTAPS Cloning

Figure 5:
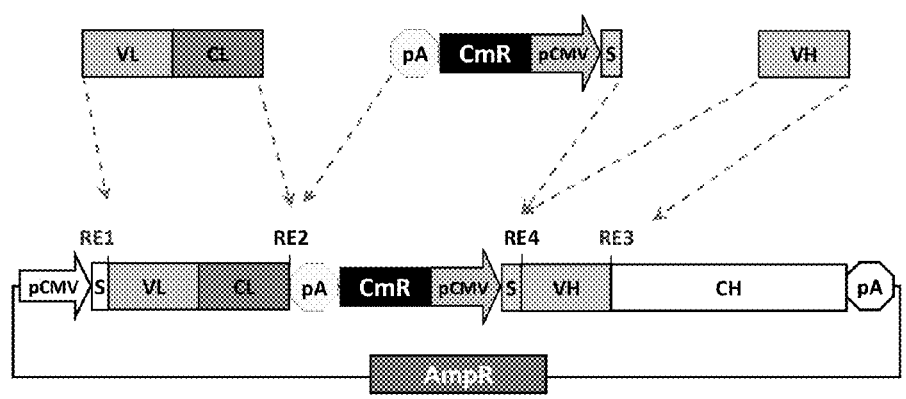
FIG. 5 Panels A and B are graphical representations depicting two examples of cloning three inserts cloned into a single vector using INTAPS cloning. The three inserts were ligated into the vector by T4 DNA ligase and the recombinant plasmids were selected with chloramphenicol. Abbreviations used in this drawing are described above.
Figure 5:
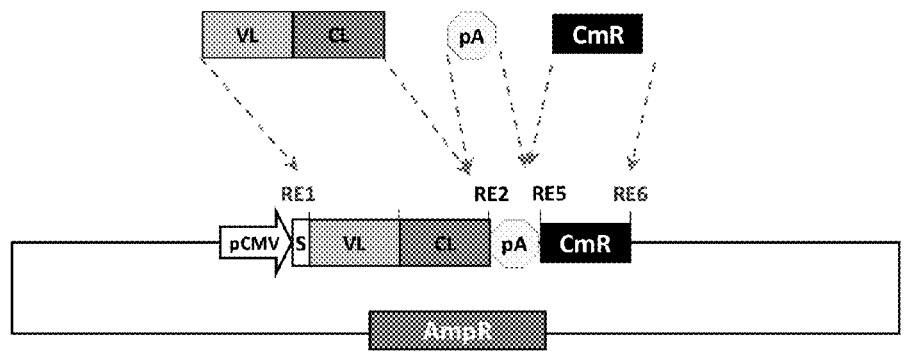

Three DNA fragments, one of which contains an INTAPS selection adaptor were digested with appropriate restriction enzymes. The fragments were ligated using T4 DNA ligase into a vector linearised with appropriate enzymes. The ligation mix was transformed into E. coli cells and selected in liquid media containing chloramphenicol. Plasmid DNA was isolated and analyzed by restriction endonuclease digestion, which confirmed the correct construct. Two examples of the application of this cloning method are depicted in FIG. 5 Panels A and 5B.

EXAMPLE 5

Cloning of Six Inserts by INTAPS Cloning

Figure 6:
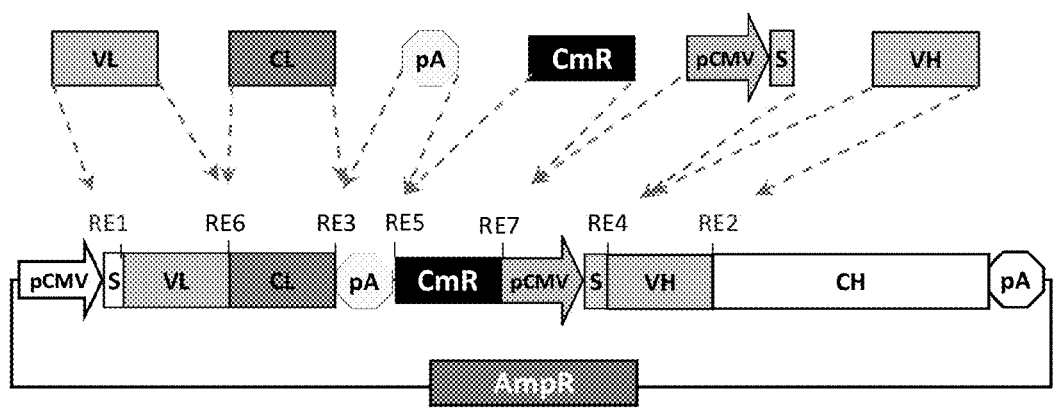
FIG. 6 is a graphical representation showing an example of cloning six inserts cloned into a single vector using INTAPS cloning. The six inserts were ligated into the vector by T4 DNA ligase and the recombinant plasmids were selected with chloramphenicol. Abbreviations used in this drawing are described above.

INTAPS has been used to clone up to six inserts into a vector in a single cloning step. Six DNA fragments, one of which contains an INTAPS selection adaptor were digested with appropriate restriction enzymes. The fragments were ligated using T4 DNA ligase into a vector linearized with appropriate enzymes. The ligation mix was transformed into E. coli cells and selected in liquid media containing chloramphenicol. Plasmid DNA was isolated and analyzed by restriction endonuclease digestion, which confirmed the correct construct. An example of the application of this cloning method is depicted in FIG. 6.

EXAMPLE 6

Fragment Swap by Using Different INTAPS Adaptors

Figure 7:
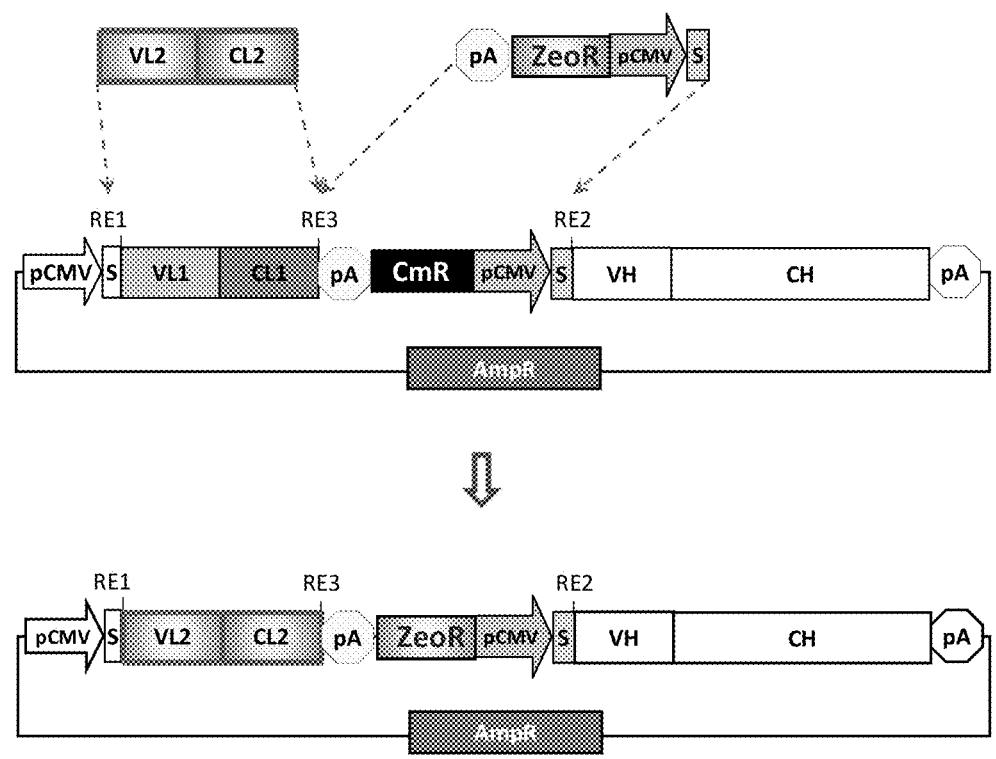
FIG. 7 is a graphical representation showing an example of swapping fragments using two different INTAPS adaptors. The light chain of an antibody-encoding expression construct was replaced by a different light chain using INTAPS cloning. The recombinant plasmid was selected using Zeocin. Abbreviations used in this drawing are described above.

A nucleic acid encoding an antibody light chain and the INTAPS adaptor with CmR marker were removed from an antibody encoding expression construct by restriction digestion. A nucleic acid encoding a new light chain and a different INTAPS adaptor encoding ZeoR marker were inserted into the vector. The recombinant construct containing the new light chain and new selection marker was selected in liquid media containing zeocin. Restriction endonuclease digestion of DNA prepared by miniprep confirmed the construct was correct. An example of the application of this cloning method is depicted in FIG. 7.

This method is also applicable to domain shuffling to improve the affinity, stability or functionality of recombinant antibodies.

EXAMPLE 7

High Throughput IgG Reformatting Using INTAPS and Ligation-Independent Cloning

The INTAPS cloning strategy was also adapted for high throughput IgG reformatting. Up to 96 clones were routinely reformatted in a single experiment. This method is easily scalable and amenable to automation. To date, over 1000 different antibody clones from phagemid constructs have been reformatted into full IgG.

Figure 8:
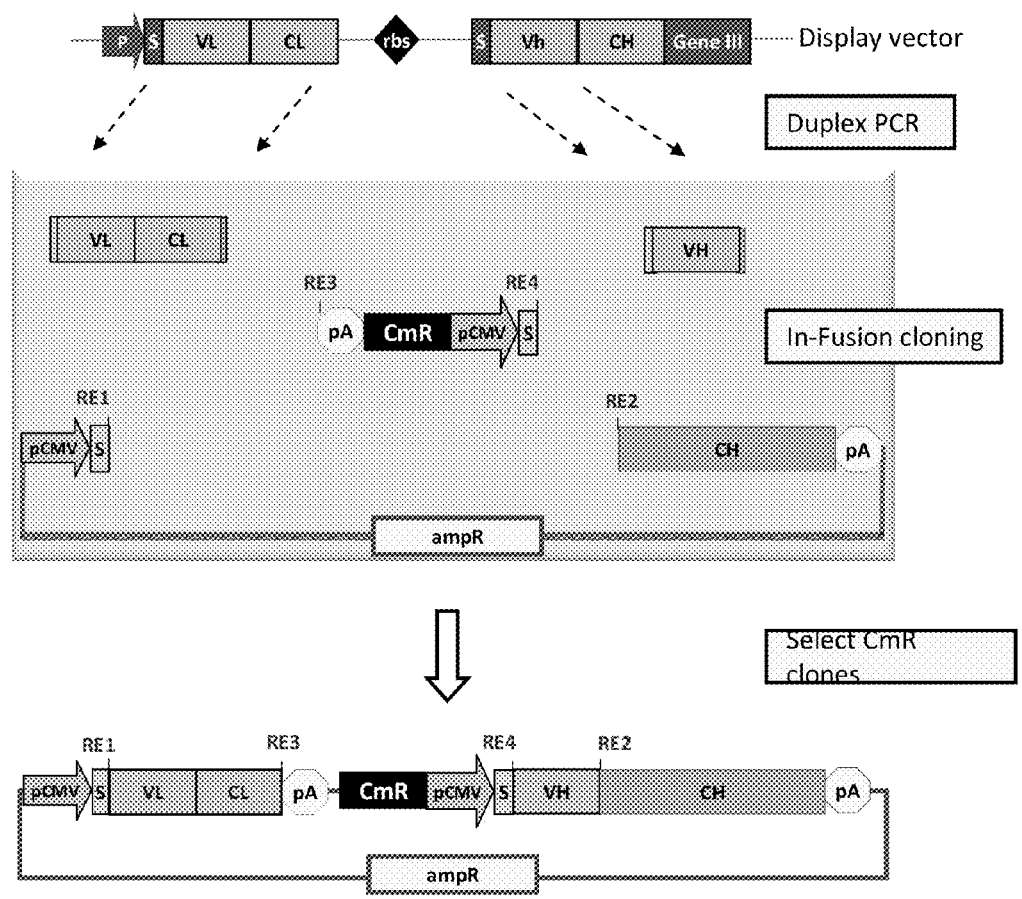
FIG. 8 is a graphical representation showing an one-step IgG reformatting strategy using INTAPS cloning in conjunction with ligation-independent cloning. The light chain and $V_H$-encoding regions were amplified from the phage display construct by Duplex-PCR. The PCR products were treated with Cloning Enhancer. The treated PCR inserts, and the pre-prepared INTAPS adaptor and expression vector were incubated with the IN-Fusion cloning enzyme. The DNA were transformed into *E. coli* and recombinant plasmids were selected in media containing chloramphenicol. Abbreviations used in this drawing are described above.

A summary of the cloning method is depicted in FIG. 8 and a description of the method follows.

7.1 Preparation of Antibody Light Chain and Variable Heavy Chain ($V_H$) Fragments The entire light chain-encoding region and $V_H$-encoding region of Fab constructs from phage display vectors were amplified from phagemids using duplex PCR. All primers utilized contained a 15 bp extension at the 5' end which is complimentary to the end of either a linearized vector or INTAPS adaptor to facilitate their ligation-independent cloning using the In-Fusion cloning kit (Clontech). PCR was performed in a 50 μl solution containing 1× AccuPrime pfx SuperMix (Invitrogen), 1 unit of AccuPrime pfx DNA polymerase, 10 ng phagemid DNA and 200 μM specific primers. The following PCR cycles were used:
1) 1×: 94° C., 3 min;
2) 5×: 93° C., 20 sec; 55° C., 20 sec; 68° C. 40 sec; and
3) 25×: 93° C., 20 sec; 62° C., 20 sec; 68° C. 40 sec.

PCR products (5 μl) were analysed by an agarose gel electrophoresis and DNA bands corresponding to the predicted sizes were obtained.

7.2 Preparation of Vector and INTAPS adaptor

The vector was linearised by digestion with appropriate restriction enzymes. The INTAPS adaptor was isolated following restriction enzyme digestion and gel-purification.

7.3 In-Fusion Cloning

In-Fusion cloning was performed essentially according to the manufacturer's instructions. Briefly, 5 μl of PCR product was incubated with 2 μl of Cloning Enhancer (Clontech) at 37° C. for 15 min and 80° C. for 15 min. A 10 μl solution containing 100 ng of linearised vector, 80 ng INTAPS adaptor and 1 μl each of the Enhancer treated light chain (LC)- and $V_H$-encoding PCR products were added to the dried-down IN-Fusion cloning kit and mixed well by pipetting. The In-Fusion solution was then incubated at 37° C. for 15 min and 50° C. for 15 min.

7.4 Transformation and Direct Recombinant Clone Selection

Following In-Fusion cloning, the resulting solution was diluted with 40 μl of TE, 5 μl of which was added to 50 μl of Top10 competent cells (Invitrogen). Following incubation on ice for 30 min, the cells were heated-shocked at 42° C. for 45 sec. SOC medium (500 μl) was added to the cells followed by incubation at 37° C. for 1 hour. The cells were then pelleted and resuspended in 5 ml of liquid broth (LB) containing 34 μg/ml chloramphenicol to directly select recombinant plasmid-containing cells.

7.5 Sequencing Analysis of Miniprep DNA

The plasmid DNA was isolated using QIAprep Spin Miniprep kit (QIAGEN) and DNA sequenced.

EXAMPLE 8

Transient Mammalian Cell Expression of IgGs

The antibody-encoding constructs described in Example 7 were transiently transfected in HEK293freestyle cells using 293fectin according to the manufacturer's instructions with some modifications. Briefly cells (30 ml) were transfected at a final concentration of $1 \times 10^6$ viable cells/ml with 10 μg purified DNA and incubated in an Infors shaking incubator for 5 days at 37° C. with an atmosphere of 5% $CO_2$. The cell culture supernatants were then harvested by centrifugation at 2500 rpm and then passed through a 0.45 μM filter (Nalgene) prior to purification using standard procedures.

EXAMPLE 9

Generation of Fc Expression Construct Using the INTAPS Adaptor

Figure 9:
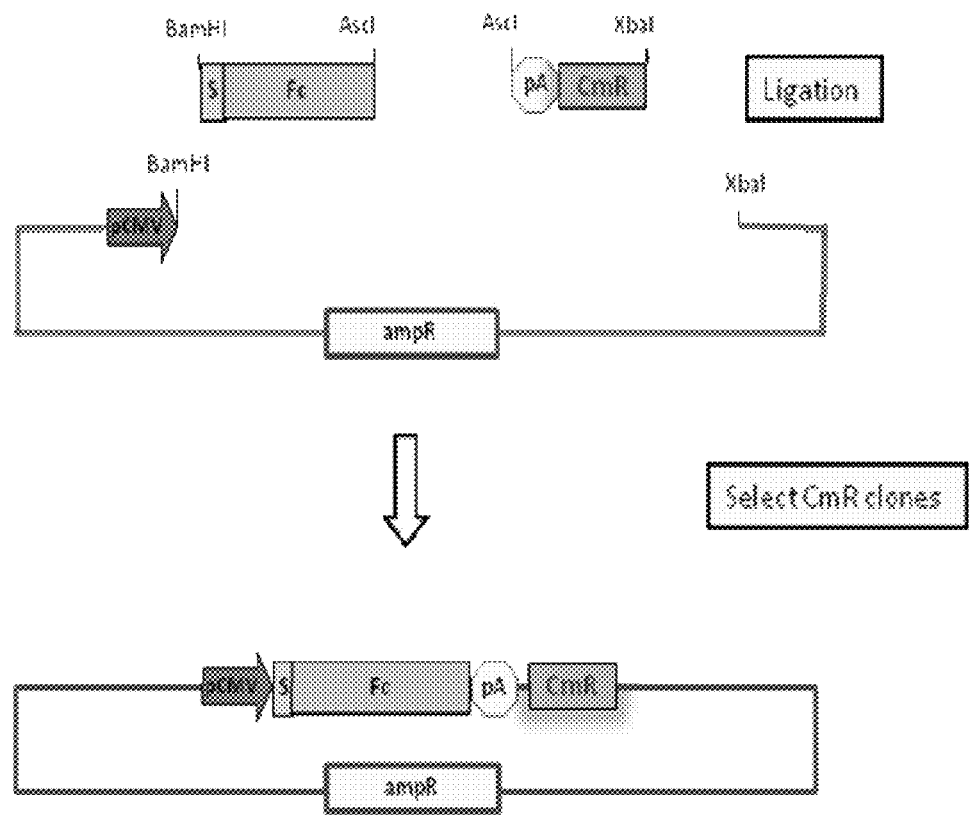
FIG. 9 is a graphical representation of one example of a process for producing an expression construct according to the present disclosure. The nucleic acid encoding a Fc polypeptide ("Fc") linked to a secretion signal ("S") (i) and a nucleic acid encoding a marker protein (in this Figure comprising a polyadenylation signal (pA) and a gene encoding a protein conferring chloramphenicol resistance (CmR)) (ii) are ligated into an expression vector (iii) (in this figure comprising a gene encoding a protein conferring ampicillin resistance (ampR), and a promoter from CMV (pCMV). After ligation, cells resistant to chloramphenicol are selected.

The expression vector pcDNA3.1 was digested with BmaHI and XbaI and gel-purified. A Fc encoding nucleic acid was amplified using PCR from a vector using primers FcF and FcR (Table 2). The BGHpA-CmR adaptor was amplified from BGHpA-CmR-CMVpro adaptor (Example 1, FIG. 2) by PCR using primers BGHpAf and CmRr (Table 2). Both PCR fragments were purified using QIAquick PCR Purification kit. The Fc encoding nucleic acid was digested with BmaHI and AscI and BGHpA-CmR encoding nucleic acid was digested with AscI and XbaI and the nucleic acids purified using QIAquick PCR Purification kit. The nucleic acids were ligated together into pcDNA3.1 linearized with BmaHI and XbaI using T4 DNA ligase (FIG. 9). DNA was transformed into Top10 competent cells as previously described and plated out onto a LB agar plate containing 34 ug/ml Chloramphenicol. Six colonies were randomly picked and grown in culture. Expression constructs were purified using QIAprep Spin Miniprep kit (QIAGEN). The miniprep DNA was digested with BamHI and XbaI and analysed by agarose gel electrophoresis which showed all 6 colonies contained the correct insert.

TABLE 2

PCR Primer sequences for Fc cloning

| Name | Sequence | SEQ ID NO |
|---|---|---|
| FcF | 5' TACCGAGCTCGGATCCGTGGCCACCATGGGATGG 3' | 13 |
| FcR | 5' GAGGCGCGCCTCATTTACCCAGAGACAGGG 3' | 14 |
| BGHpAf: | 5' AATGAGGCGCGCCTCGACTGTGCCTTCTAG 3' | 15 |
| CmRr | 5' AAACGGGCCCTCTAGATTACGCCCCGCCCTGCCA 3' | 16 |

The invention claimed is:

1. A method for producing an expression construct capable of expressing a plurality of polypeptides, the method comprising:
   providing the following unlinked nucleic acids:
   (i) a first nucleic acid encoding a first polypeptide;
   (ii) a second nucleic acid encoding a second polypeptide; and
   (iii) a third nucleic acid encoding a marker protein that facilitates detection and/or isolation of a cell expressing the marker protein;
   providing an expression vector, which does not comprise a nucleic acid encoding the marker protein encoded by the nucleic acid at (iii); and
   linking said unlinked nucleic acids and said expression vector in a single cloning cycle, wherein said linking comprises ligase dependent cloning or ligase independent cloning, and wherein said first polypeptide and said second polypeptide associate to form a multimeric protein.

2. The method of claim 1, wherein the nucleic acids are linked together using ligase independent cloning.

3. The method of claim 1, wherein the expression vector comprises a nucleic acid encoding a further polypeptide that is expressed as a fusion with at least one of the polypeptides.

4. The method of claim 1, wherein the nucleic acid(s) encoding the polypeptide(s) are each operably linked to a promoter.

5. The method of claim 4, wherein the nucleic acid encoding the marker protein further comprises a promoter that becomes operably linked to at least one of the nucleic acids encoding a polypeptide.

6. The method of claim 1, wherein the marker protein confers resistance to a toxic compound on a cell in which it is expressed or is a fluorescent protein or is a protein that metabolizes a substrate to produce a detectable compound or is a protein that confers a growth advantage on an auxotrophic cell.

7. The method of claim 1, wherein the polypeptides each comprise an antibody variable region.

8. The method of claim 7 comprising linking the following unlinked nucleic acids:
   (i) a nucleic acid encoding an antibody heavy chain variable region ($V_H$);
   (ii) a nucleic acid encoding a marker protein that facilitates detection and/or isolation of a cells expressing the marker protein and a promoter; and
   (iii) an expression vector comprising a sequence encoding one or more antibody heavy chain constant regions, wherein the vector does not comprise a nucleic acid encoding the marker protein encoded by the nucleic acid at (ii);
   such that:
   (a) the promoter and the nucleic acid encoding the $V_H$ are operably linked; and
   (b) the nucleic acid encoding the $V_H$ and the sequence encoding one or more antibody heavy chain constant regions are linked so as to encode a functional fusion protein.

9. The method of claim 7 comprising linking the following unlinked nucleic acids:
   (i) a nucleic acid encoding an antibody light chain variable region ($V_L$) and, optionally a sequence encoding a light chain constant region positioned 3' to the sequence encoding the $V_L$;
   (ii) a nucleic acid encoding a marker protein that facilitates detection and/or isolation of a cells expressing the marker protein; and
   (iii) an expression vector comprising a promoter, wherein the vector does not comprise a nucleic acid encoding the marker protein encoded by the nucleic acid at (ii), such that:
   (a) the promoter and the nucleic acid encoding the $V_L$ are operably linked; and
   (b) the nucleic acid encoding the marker protein is positioned between the nucleic acid encoding the $V_L$ and the expression vector.

10. The method of claim 9, wherein the nucleic acid encoding the marker protein comprises a polyadenylation signal, which following linking of the nucleic acids is operably linked to the nucleic acid encoding the $V_L$.

11. The method of claim 7 comprising linking the following unlinked nucleic acids:
    (i) a first nucleic acid encoding an antibody light chain variable region and a light chain constant region;
    (ii) a nucleic acid encoding a marker protein that facilitates detection and/or isolation of a cells expressing the marker protein and a first promoter;
    (iii) a second nucleic acid encoding an antibody heavy chain variable region; and
    (iv) an expression vector comprising a sequence encoding one or more antibody heavy chain constant regions and a second promoter, wherein the vector does not comprise a nucleic acid encoding the marker protein encoded by the nucleic acid at (ii);
    such that:
    (a) the second promoter and first nucleic acid are operably linked;
    (b) the nucleic acid encoding the marker protein is positioned between the first and second nucleic acids such that the first promoter is operably linked to the second nucleic acid;
    (c) the second nucleic acid and said sequence encoding one or more antibody heavy chain constant regions are linked so as to encode a functional fusion protein.

12. The method of claim 1, wherein the first polypeptide comprises an antibody light chain variable region ($V_L$) and, optionally an antibody light chain constant region and the second polypeptide comprises an antibody heavy chain variable region ($V_H$).

13. The method of claim 1, further comprising performing the method a plurality of times in parallel, to thereby produce a plurality of expression constructs.

14. A method for producing a nucleic acid construct capable of expressing a plurality of polypeptides comprising:
    providing the following unlinked nucleic acids:
    (i) a first nucleic acid encoding a first polypeptide;
    (ii) a second nucleic acid encoding a marker protein that facilitates detection and/or isolation of a cell expressing the marker protein; and
    (iii) a third nucleic acid encoding a second polypeptide; and
    linking said unlinked nucleic acids in a single cloning cycle, such that the second nucleic acid encoding the marker protein is positioned between the first and third nucleic acids, wherein said linking comprises ligase dependent cloning or ligase independent cloning, wherein said linking of said first, said second and said third nucleic acid forms said nucleic acid construct, and wherein said first polypeptide and said second polypeptide associate to form a multimeric protein.

15. The method of claim 14, further comprising inserting the linked nucleic acids into an expression vector.

16. A process for producing a cell expressing a multimeric protein comprising:
   (i) producing an expression construct in accordance with the method set forth in claim 1;
   (ii) introducing the expression construct into a cell; and
   (iii) selecting a cell comprising the expression construct.

17. The process of claim 16, wherein the marker protein of step (i) confers resistance to a toxic compound on a cell in which it is expressed, and said selecting a cell comprising the expression construct comprises exposing the cell to the toxic compound.

18. The process of claim 16, wherein each of steps (i), (ii) and (iii) are performed in solution in a single reaction vessel.

19. The process of claim 18, wherein each of steps (i), (ii) and (iii) are performed without culturing cells on a solid medium.

20. A process for producing a multimeric protein comprising:
   (i) producing an expression construct in accordance with the method set forth in claim 1;
   (ii) maintaining the expression construct under conditions such that the multimeric protein is expressed to thereby produce the multimeric protein; and
   (iii) optionally, purifying the multimeric protein.

21. The process of claim 20, wherein the multimeric protein comprises an antibody variable region.

\* \* \* \* \*

SEQUENCE LISTING

<160> NUMBER OF SEQ ID NOS: 16

<210> SEQ ID NO 1
<211> LENGTH: 28
<212> TYPE: DNA
<213> ORGANISM: artificial
<220> FEATURE:
<223> OTHER INFORMATION: primer for amplifying bGH pA

<400> SEQUENCE: 1
aaaggcgcgc ctcgactgtg ccttctag                                    28

<210> SEQ ID NO 2
<211> LENGTH: 38
<212> TYPE: DNA
<213> ORGANISM: artificial
<220> FEATURE:
<223> OTHER INFORMATION: primer for amplifying bGH pA and CmRF

<400> SEQUENCE: 2
gatgcggtgg gctctatggc tgaacgagaa acgtaaaa                         38

<210> SEQ ID NO 3
<211> LENGTH: 38
<212> TYPE: DNA
<213> ORGANISM: artificial
<220> FEATURE:
<223> OTHER INFORMATION: primer for amplifying BGH/CmR

<400> SEQUENCE: 3
ttttacgttt ctcgttcagc catagagccc accgcatc                         38

<210> SEQ ID NO 4
<211> LENGTH: 37
<212> TYPE: DNA
<213> ORGANISM: artificial

```
<220> FEATURE:
<223> OTHER INFORMATION: primer for amplifying CmR/pCMV

<400> SEQUENCE: 4
tggcagggcg gggcgtaagt tgacattgat tattgac                              37

<210> SEQ ID NO 5
<211> LENGTH: 37
<212> TYPE: DNA
<213> ORGANISM: artificial
<220> FEATURE:
<223> OTHER INFORMATION: primer for amplifying CmR/pCMV

<400> SEQUENCE: 5
gtcaataatc aatgtcaact tacgccccgc cctgcca                              37

<210> SEQ ID NO 6
<211> LENGTH: 39
<212> TYPE: DNA
<213> ORGANISM: artificial
<220> FEATURE:
<223> OTHER INFORMATION: primer for amplifying CMV/SP

<400> SEQUENCE: 6
tacgactcac tatagggccg ccaccatggg atggagctg                            39

<210> SEQ ID NO 7
<211> LENGTH: 39
<212> TYPE: DNA
<213> ORGANISM: artificial
<220> FEATURE:
<223> OTHER INFORMATION: primer for amplifying CMV/SP

<400> SEQUENCE: 7
cagctccatc ccatggtggc ggccctatag tgagtcgta                            39

<210> SEQ ID NO 8
<211> LENGTH: 20
<212> TYPE: DNA
<213> ORGANISM: artificial
<220> FEATURE:
<223> OTHER INFORMATION: primer for amplifying VH/SP

<400> SEQUENCE: 8
gctgtgcact ccagtagctg                                                 20

<210> SEQ ID NO 9
<211> LENGTH: 37
<212> TYPE: DNA
<213> ORGANISM: artificial
<220> FEATURE:
<223> OTHER INFORMATION: primer for amplifying bGH/ZeoR

<400> SEQUENCE: 9
gatgcggtgg gctctatggg cctgatgcgg tattttc                              37

<210> SEQ ID NO 10
<211> LENGTH: 36
<212> TYPE: DNA
<213> ORGANISM: artificial
<220> FEATURE:
<223> OTHER INFORMATION: primer for amplifying bGH/ZeoR

<400> SEQUENCE: 10
gagaaaatac cgcatcaggc catagagccc accgca                               36
```

<210> SEQ ID NO 11
<211> LENGTH: 36
<212> TYPE: DNA
<213> ORGANISM: artificial
<220> FEATURE:
<223> OTHER INFORMATION: primer for amplifying ZeoR/CMV

<400> SEQUENCE: 11
gccgaggagc aggactgacg ttgacattga ttattg         36

<210> SEQ ID NO 12
<211> LENGTH: 36
<212> TYPE: DNA
<213> ORGANISM: artificial
<220> FEATURE:
<223> OTHER INFORMATION: primer for amplifying ZeoR/pCMV

<400> SEQUENCE: 12
tggcagggcg gggcgtaagt tgacattgat tattga         36

<210> SEQ ID NO 13
<211> LENGTH: 34
<212> TYPE: DNA
<213> ORGANISM: artificial
<220> FEATURE:
<223> OTHER INFORMATION: primer for amplifying Fc

<400> SEQUENCE: 13
taccgagctc ggatccgtgg ccaccatggg atgg         34

<210> SEQ ID NO 14
<211> LENGTH: 30
<212> TYPE: DNA
<213> ORGANISM: artificial
<220> FEATURE:
<223> OTHER INFORMATION: primer for amplifying Fc

<400> SEQUENCE: 14
gaggcgcgcc tcatttaccc agagacaggg         30

<210> SEQ ID NO 15
<211> LENGTH: 30
<212> TYPE: DNA
<213> ORGANISM: artificial
<220> FEATURE:
<223> OTHER INFORMATION: primer for amplifying bGHpA

<400> SEQUENCE: 15
aatgaggcgc gcctcgactg tgccttctag         30

<210> SEQ ID NO 16
<211> LENGTH: 34
<212> TYPE: DNA
<213> ORGANISM: artificial
<220> FEATURE:
<223> OTHER INFORMATION: primer for amplifying CmR

<400> SEQUENCE: 16
aaacgggccc tctagattac gccccgccct gcca         34